United States Patent
Rezvani et al.

(10) Patent No.: US 10,517,919 B2
(45) Date of Patent: Dec. 31, 2019

(54) SELECTIVE NOX-1 INHIBITOR PEPTIDES AND USES THEREOF

(71) Applicants: UNIVERSITE DE BORDEAUX, Bordeaux (FR); INSERM, Paris (FR)

(72) Inventors: Hamid Reza Rezvani, Merignac (FR); Frédéric Mazurier, Neuillé-Pont-Pierre (FR); Alain Taieb, Bordeaux (FR); L'Emira Ghida Harfouche, Hazmieh New Mar Takla (LB)

(73) Assignees: Universite de Bordeaux (FR); INSERM (FR)

( * ) Notice: Subject to any disclaimer, the term of this patent is extended or adjusted under 35 U.S.C. 154(b) by 42 days.

(21) Appl. No.: 15/667,737

(22) Filed: Aug. 3, 2017

(65) Prior Publication Data

US 2017/0340697 A1    Nov. 30, 2017

Related U.S. Application Data

(63) Continuation of application No. 14/758,991, filed as application No. PCT/EP2014/050063 on Jan. 3, 2014, now abandoned.

(30) Foreign Application Priority Data

Jan. 3, 2013 (EP) .................................. 13150187

(51) Int. Cl.
*A61K 38/08* (2019.01)
*A61K 38/00* (2006.01)
(Continued)

(52) U.S. Cl.
CPC .............. *A61K 38/08* (2013.01); *A61K 8/64* (2013.01); *A61K 38/005* (2013.01); *A61K 38/44* (2013.01);
(Continued)

(58) Field of Classification Search
None
See application file for complete search history.

(56) References Cited

U.S. PATENT DOCUMENTS

| 6,551,795 B1 | 4/2003 | Rubenfield et al. |
| 2003/0125249 A1 | 7/2003 | Blecha |

(Continued)

FOREIGN PATENT DOCUMENTS

| GB | 2 285 047 A | 6/1995 |
| WO | 91/17763 A1 | 11/1991 |

(Continued)

OTHER PUBLICATIONS

Altenhofer et al., 2015, "Evolution of NADPH Oxidase Inhibitors: Selectivity and Mechanisms for Target Engagement", Anttioxidants & Redox Signaling, 23(5):406-427.

(Continued)

*Primary Examiner* — Kevin S Orwig
(74) *Attorney, Agent, or Firm* — Law Offices of Albert Wai-Kit Chan, PLLC

(57) ABSTRACT

The present invention relates to novel peptides, compositions and methods for the prevention and/or treatment of pathological conditions and diseases associated with NADPH oxidase 1 (Nox1) activity, and/or increased reactive oxygen species (ROS) production. The novel peptides are thus particularly useful for treating and/or preventing cancer, atherosclerosis, angiogenesis, and aging.

14 Claims, 16 Drawing Sheets
Specification includes a Sequence Listing.

|  | Sequences |
|---|---|
| Control peptide 1 (SEQ ID NO : 57) (scramble) | RKK RRQ RRR VTP TRP PSR |
| Peptide A (+tat) (SEQ ID NO : 41) | RKK RRQ RRR PPT VPT RPS |
| Peptide A (-tat) (SEQ ID NO : 20) | PPT VPT RPS |
| P8: Shorter peptide A (-tat) (SEQ ID NO : 56) | PPT VPT RP |
| P7: Shorter peptide A (-tat) (SEQ ID NO : 2) | PPT VPT R |

(51) Int. Cl.
     A61K 8/64      (2006.01)
     A61Q 17/04     (2006.01)
     A61K 47/64     (2017.01)
     A61K 38/44     (2006.01)
     C12N 9/02      (2006.01)
     A61Q 19/08     (2006.01)

(52) U.S. Cl.
     CPC ............ *A61K 47/645* (2017.08); *A61Q 17/04* (2013.01); *A61Q 19/08* (2013.01); *C12N 9/0036* (2013.01); *C12Y 106/03001* (2013.01); *A61K 2800/782* (2013.01)

(56) References Cited

U.S. PATENT DOCUMENTS

| | | |
|---|---|---|
| 2007/0098706 A1 | 5/2007 | Valente |
| 2010/0119533 A1 | 5/2010 | Clancy et al. |
| 2014/0357549 A1 | 12/2014 | Ranayhossaini et al. |

FOREIGN PATENT DOCUMENTS

| | | |
|---|---|---|
| WO | 95/03819 A1 | 2/1995 |
| WO | 95/24419 | 9/1995 |
| WO | 97/30074 A1 | 8/1997 |
| WO | 2008/109833 A2 | 9/2008 |

OTHER PUBLICATIONS

Cifuentes-Pagano et al., 2015, "Nox Inhibitors & Therapies: Rational Design of Peptidic and Small Molecule Inhibitors", Curr Pharm Des., 21(41):6023-6035.

Drummond et al., 2011, "Combating oxidative stress in vascular disease: NADPH oxidases as therapeutic targets", Nature Reviews, 10:453-471.

El-Benna et al., 2012, "Towards specific NADPH oxidase inhibition by small synthetic peptides", Cellular and Molecular Life Sciences, 69:2307-2314.

Mousslim et al., 2017, "Peptide screen identifies a new NADPH oxidase inhibitor: impact on cell migration and invasion", European Journal of Pharmacology, 794:162-172.

Raad et al., 2017, "NADPH Oxidase-1 Plays a Key Role in Keratinocyte Responses to UV Radiation and UVB-Induced Skin Carcinogenesis", Journal of Investigative Dermatology, 137:1311-1321 (Published Online as doi:10.1016/j.jid.2016.12.027).

Ranayhossaini et al., 2013, "Selective Recapitulation of Conserved and Nonconserved Regions of Putative NOXA1 Protein Activation Domain Confers Isoform-specific Inhibition of Nox1 Oxidase and Attenuation of Endothelial Cell Migration", Journal of Biological Chemistry, 288(51):36437-36450.

Schramm et al., 2012, "Targeting NADPH oxidases in vascular pharmacology", Vascular Pharmacology, 56:216-231.

Teixeira et al., 2017, "Therapeutic potential of NADPH oxidase 1/4 inhibitors", British Journal of Pharmacology, 174:1647-1669.

Valente Anthony J et al., 2007, "NOX1 NADPH oxidase regulation by the NOXA1 SH3 domain", Free Radical Biology & Medicine, 43(3):384-396.

PCT Written Opinion, dated Mar. 7, 2015, for Universite Bordeaux Segalen, International Application No. PCT/2014/050063.

International Search Report, dated Mar. 31, 2014, for Universite Bordeaux Segalen, International Application No. PCT/2014/050063.

International Preliminary Report on Patentability, dated Jul. 7, 2015, for Universite de Bordeaux, International Application No. PCT/EP2014/050063.

European Search Report, dated May 21, 2013, for Universite Bordeaux Segalen, et al, European Application No. EP 13 15 0187.

European Opinion, dated May 29, 2013, for Universite Bordeaux Segalen, et al, European Application No. EP 13 15 0187.

Chinese Office Action, dated May 5, 2016, for Universite de Bordeaux, China Application No. 201480003978.1.

U.S. Office Action, dated Mar. 17, 2016, for Universite de Bordeaux, U.S. Appl. No. 14/758,991.

U.S. Office Action, dated Jun. 28, 2016, for Universite de Bordeaux, U.S. Appl. No. 14/758,991.

U.S. Office Action, dated Oct. 12, 2016, for Universite de Bordeaux, U.S. Appl. No. 14/758,991.

Chinese Office Action, dated Jan. 22, 2017, for Universite de Bordeaux, China Application No. 201480003978.1.

| | Sequences |
|---|---|
| Control peptide 1 (SEQ ID NO : 57) (scramble) | RKK RRQ RRR VTP TRP PSR |
| Peptide A (+tat) (SEQ ID NO : 41) | RKK RRQ RRR PPT VPT RPS |
| Peptide A (-tat) (SEQ ID NO : 20) | PPT VPT RPS |
| P8: Shorter peptide A (-tat) (SEQ ID NO : 56) | PPT VPT RP |
| P7: Shorter peptide A (-tat) (SEQ ID NO : 2) | PPT VPT R |

SELECTIVE NOX-1 INHIBITOR PEPTIDES AND USES THEREOF

CROSS-REFERENCE TO RELATED APPLICATIONS

This application is a Continuation Application of U.S. Ser. No. 14/758,991, filed Jul. 2, 2015, which is a National Stage of Int'l App'l No. PCT/EP2014/050063, filed Jan. 3, 2014, which claims the benefit of European application No. 13150187.6, filed Jan. 3, 2013. The entire contents and disclosures of the preceding applications are hereby incorporated by reference into this application.

FIELD OF INVENTION

The invention relates to novel peptides, compositions and methods for the prevention and/or treatment of pathological conditions and diseases associated with NADPH oxidase 1 (Nox1) activity, and/or increased reactive oxygen species (ROS) production. The novel peptides are thus particularly useful for treating and/or preventing cancer, atherosclerosis, angiogenesis, and aging.

BACKGROUND OF THE INVENTION

Nox1 generates ROS in physiological conditions and certain pathological conditions. ROS are known to contribute to damage within organisms and are thus associated with many different conditions. NADPH oxidases are also known as a source of oxidative stress, which contributes to the cause of many conditions. Nox1 expression is known to be associated with many different conditions, including cancers.

Therapeutic selectivity without toxicity is clearly important in a therapeutic agent. In particular preferential killing of cancer cells without toxicity to normal cells, is one of the most important considerations in cancer therapy.

Prior to the present invention, several inhibitors of NADPH oxidases (Nox) have been identified, but so far no specific Nox inhibitors have been developed.

Several cell-permeable peptide inhibitors, such as gp91ds-tat peptide, PR-39, as well as Rac peptide inhibitors have been also tested. The gp91ds-tat peptide was designed to inhibit specifically Nox2 by mimicking a sequence of Nox2 that is thought to be important for the interaction with p47phox. However, the peptide lacked specificity since the region targeted by the peptide is homologous in other NOX isoforms. In addition, the peptide had a low-efficacy inhibitor, inhibiting neutrophil ROS generation by 25% at 50 mM.

Recently, the company GenKyoTex developed more specific Nox inhibitors using Pyrazolo-pyrido-diazepine, -pyrazine and -oxazine dione derivatives, targeting in particular Nox1 and Nox4 enzymes. GenKyoTex is currently conducting a Phase I clinical with a small molecule, GKT137831 for the treatment of diabetic nephropathy. Preclinical experiments are also conducted for the treatment of diabetic nephropathy, atherosclerosis, idiopathic pulmonary fibrosis, liver fibrosis and models of angiogenesis. However, while being specific for Nox1/Nox4, GKT137831 also shows affinity for Nox2, Nox3, and Nox5, and thus has a low selectivity.

Other chemical compounds have been used for many years, including apocynin, diphenylene iodonium (DPI), and 4-(2-aminoethyl)-benzensulfonyl fluoride hydrochloride (AEBSF) and neopterin.

Apocynin, which was extracted from *Picrorhiza kurroa*, can prevent the formation of the active oxidase complex. The inhibitory effect of apocynin is however controversial. In fact, it was shown that apocynin is not specific for NADPH oxidases, but rather influences other events such as Thromboxane A2 formation and the induction of AP-1 transcription factor, and that it is an antioxidant, rather than a Nox enzyme inhibitor.

Diphenylene iodonium (DPI) is an unspecific inhibitor of all flavoenzymes, and thus can inhibit the Nox enzymes, but also xanthine oxidase and cytochrome P450 enzymes. In addition of being non-selective, DPI has been showed to be toxic. It is also an inhibitor of acetylcholinesterase and butyrylcholinesterase as well as of the internal $Ca^{2+}$ pump, which in addition to its intrinsic toxicity raises major concerns on its application.

Aminoethyl-benzenesulfono-fluoride (AEBSF) has been shown to prevent the binding of flavocytochrome $b_{558}$ to $p47^{phox}$, the activation of the NADPH oxidase and the elicitation of $O_{·2}^-$ production in macrophages. AEBSF is however primarily a serine protease inhibitor; it is thus capable of inhibiting with a higher efficiency proteases such as chymotrypsin, kallikrein; plasmin, thrombin, and trypsin, and has many additional effects.

Some other non-specific molecules, misleadingly named as indirect Nox inhibitors, have been shown to interfere with the upstream signal-transduction pathways affecting Nox enzymes. These include the VAS2870 which is a thiotriazolopyrimidine compound which inhibits PDGF-dependent Src activation of Nox enzymes, angiotensin converting enzyme inhibitors (ACE inhibitors), Ang II receptor blockers (ARBs), phosphodiesterase, eicosanoids, corticosteroids, MAP kinase, protein kinase C inhibitors (such as a benzo (b)pyran-4-one derivative, S17834 of Shionogi Pharma).

There are also an increasing number of reports using siRNA approaches directed against the Nox enzymes. Specifically some RNAi has been developed to knockdown Nox1 expression. However, the use of RNAi as a therapeutic intervention for humans is still in its infancy, and may take years to optimize. Unfortunately, only a few of the siRNAs have been properly tested for specificity of Nox isoforms. There are not any satisfactory siRNA approaches for selective inhibition of Nox, specifically Nox1.

Therefore the compounds which have been developed so far are not acting directly to block the enzyme, but either interfere with the upstream transduction pathway, or act as antioxidants or ROS scavengers. The only compounds that are capable of directly blocking the enzyme, however lack selectivity and inhibit other enzymatic activities. They also have low potency and bioavailability, thereby precluding a pharmacologic demonstration of Nox as therapeutic targets in vivo. Several small-molecule and peptide inhibitors of the Nox enzymes have been useful in experimental studies, but issues of specificity and toxicity militate against any of the existing compounds as candidates for drug development.

Given the broad array of disease targets documented in recent work, it was critical to find novel clinically useful inhibitors of the Nox enzymes. The greatest challenge was however the discovery of peptide inhibitors which are capable of acting specifically on individual Nox isoforms.

The Applicant has undertaken and successfully achieved this challenge. Indeed, the present invention provides novel peptide inhibitors that block directly and specifically NADPH oxidase-1 (Nox1) assembly, without inhibiting other NADPH noxidases, particularly Nox2, Nox4, Nox5, Duox1, and Duox2. Nox1 is involved in the development and progression of a wide spectrum of diseases, including cancer, aging, neurodegenerative diseases, and cardiovascular diseases, and thus represents a significant therapeutic target. The novel peptides according to the present invention are thus also particularly advantageous as they do not have non-specific ROS scavenging or antioxidant activity and they do not inhibit other sources of ROS. Compared to RNAi technology, the peptide inhibitors are very specific for their target protein, thereby reducing the likelihood of off-target effect. When compared to chemical inhibitors, the peptides according to the present invention showed no toxic effect in vivo. Furthermore, they are easy to design and produce.

SUMMARY OF THE INVENTION

The present invention thus provides a peptide per se comprising an amino acid sequence comprising at least 7 to 35 continuous amino acids, comprising a portion of the following amino acid general sequence X1-P-X2-X3-P-X4-R (SEQ ID NO: 1), wherein X1 is A, P or Q; X2 is P, T, V, A, S, C, M or K; X3 is L, I, V or A, and X4 is T, V, S, A, M. Such peptides are particularly useful in a method of preventing and/or treating a pathological condition or disease associated either with Nox1 activity and/or increased reactive oxygen species (ROS) production.

The present invention is directed towards novel selective peptides which are capable of selectively inhibiting Nox1 activation, and are designated hereinafter Nox1 inhibitor peptides. These novel peptides are thus useful as medicament, as photoprotection agent and/or as anti-aging agent. They may optionally be conjugated to a cell penetrating peptide or an agent which increases the accumulation of said peptide in a cell (cell carrier).

According to a first embodiment, the present invention concerns compositions comprising an effective amount of the Nox1 inhibitor peptides according to the present invention, as well as pharmaceutical compositions comprising a therapeutically effective amount of the Nox1 inhibitor peptides and a pharmaceutically acceptable vehicle or excipient, and cosmetic compositions.

The novel Nox1 inhibitor peptides and compositions according to the present invention may be advantageously be used in a method of treating and/or preventing of oxygen-radical mediated diseases, and more specifically NADPH Oxidase-1/Nox1 related disorders, including cardiovascular disorders, angiogenesis-dependant disorders, respiratory disorders, skin disorders, neurodegenerative disorders, allergic and autoimmune disorders, gastrointestinal disorders, cancers, and diseases related to impaired metabolism. Most particularly, they are useful in a method of treating and/or preventing vascular and cardiovascular diseases, cancer diseases, such as colon cancer and skin cancer, as well as skin disorders, UV skin damage, skin conditions due to aging, ROS induced skin damage, premature aging, and/or skin tumorigenesis following UV exposition (UV A or UV B).

According to a second embodiment, the present invention relates to a method of decreasing the levels of reactive oxygen species (ROS) and/or inhibiting production of reactive oxygen species (ROS) in a subject in need, and particularly a method of selectively reducing and/or inhibiting NADPH oxidase 1 (Nox1) activity comprising administering a therapeutically effective amount of the novel Nox1 inhibitor peptides or compositions.

According to a third embodiment, the present invention concerns a method of treating and/or preventing oxygen-radical mediated diseases, and more specifically NADPH Oxidase-1/Nox1 related disorders, including cardiovascular disorders, angiogenesis-dependant disorders, respiratory disorders, skin disorders, neurodegenerative disorders, allergic and autoimmune disorders, gastrointestinal disorders, cancers such as colon cancers and skin cancers, and diseases related to impaired metabolism. The methods of the present invention are also useful for treating and/or preventing skin disorders, UV skin damage, skin conditions due to aging, ROS induced skin damage, premature aging and/or skin tumorigenesis following UV exposition (UV A or UV B).

According to a fourth embodiment, the present invention relates to a process for preparing the novel peptides as well as peptides which are optionally conjugated to a cell penetrating peptide or a cell carrier.

BRIEF DESCRIPTION OF THE FIGURES

As shown in FIGS. 1A and 1B, human keratinocytes were treated with different concentrations of the peptides A (SEQ ID NO: 41), B (SEQ ID NO: 42), and C (SEQ ID NO: 43) and the viability was measured 24, 48 and 72 hours post-treatment using the trypan blue dye (A) and the MTT assay (B). The percentage of viability in treated keratinocytes was normalized to the non-treated cells (NTC).

FIG. 3A shows that both shNox1 and shNox2 stably inhibited more than 80% of Nox1 and Nox2 expression, respectively. Transduction efficacy was checked by western blotting analysis. Relative ROS level (3B) and Nox activity (3C) were measured 24 h post-treatment with Nox1 inhibitor peptide A compared to control peptide C. ROS level was normalized to counterpart peptide C-treated cells. NADPH oxidase activity was measured by relative luminescence unit (RLU) per µg of proteins. *P<0.05. As per FIG. 3B measurement of ROS level revealed that treatment with peptide inhibitor A had no effect on steady-state levels of ROS in shNox1-transduced cells, indicating that peptide A blocked Nox1-dependent ROS generation with very high (near 100%) efficiency and specificity. In FIG. 3C NADPH oxidase activity was measured in shCtrl and shNox1-transduced cells treated with or without Nox1 inhibitor peptide A.

Figure 5A:
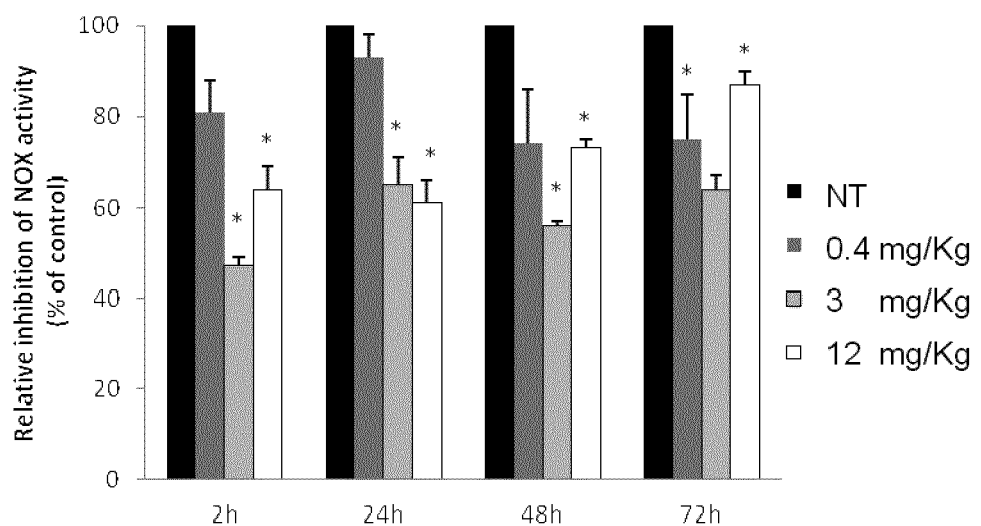
Figure 5B:
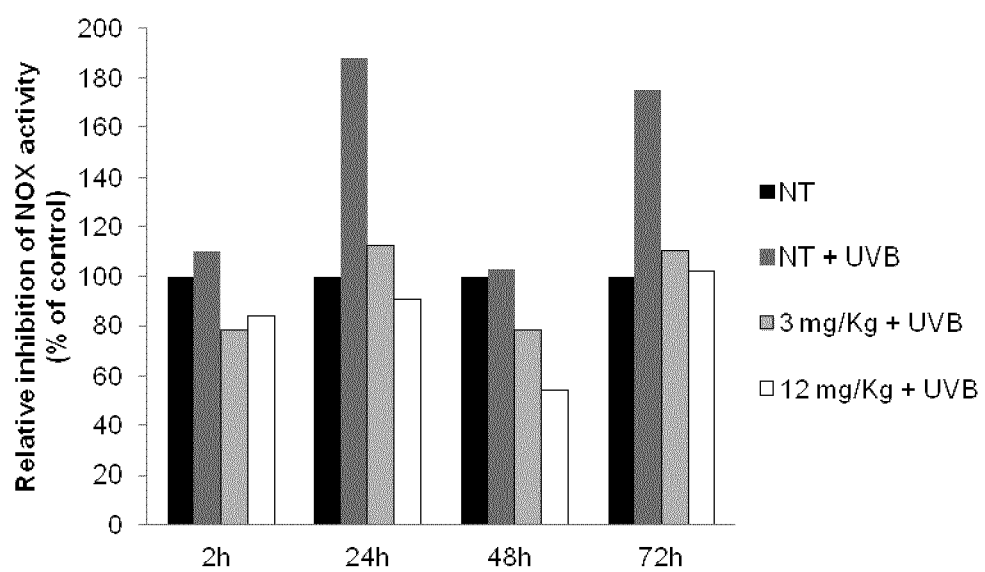

FIGS. 5A and 5B: show effect of peptide A on Nox1 activity in mouse skin. SKH-1 mice were treated topically with different doses: 0.4, 3 and 12 mg/kg (3 mice per dose) of Nox1 inhibitor peptide A. Skin biopsies were harvested 2 h, 24 h, 48 h and 72 h post-treatment and the NADPH oxidase activity was measured (RLU/µg of proteins). Results was normalized to the non-treated (NT) mice and expressed as % of inhibition of Nox activity. (B) Mice were treated topically with 3 and 12 mg/kg of peptide A (2 mice per dose). 10 min after treatment, mice were exposed to UVB (150 mJ/cm$^2$). Skin biopsies were harvested 2 h, 24 h. At 46 h after first treatment, mice were treated again with the same concentration of peptide A and exposed to UVB 10 min later. Skin biopsies were then harvested at 2 h, 24 h (i.e. 48 and 72 h after first treatment, respectively). The NADPH oxidase activity was measured (RLU/µg of proteins) and was normalized to the non-treated (NT) and non-irradiated mice.

Figure 6A:
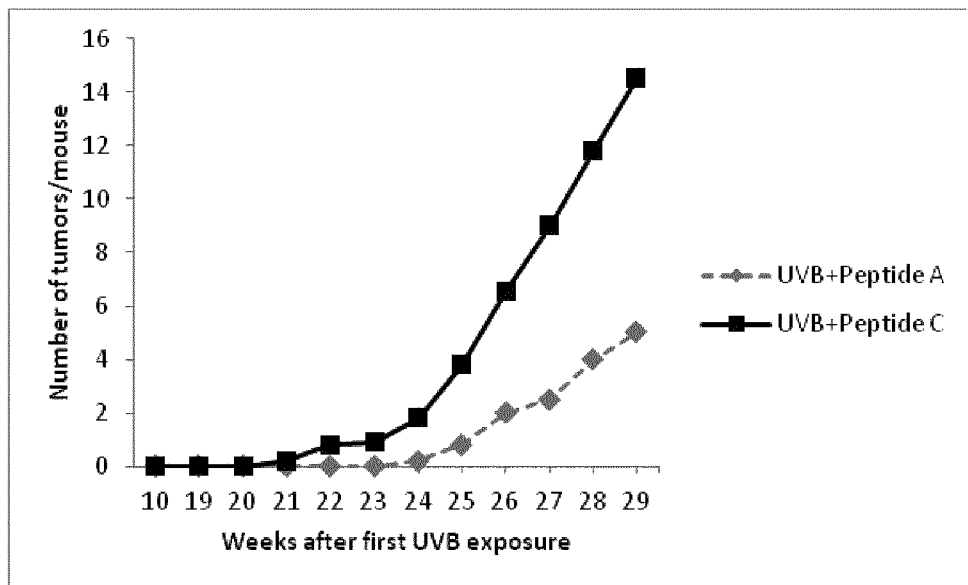
Figure 6B:
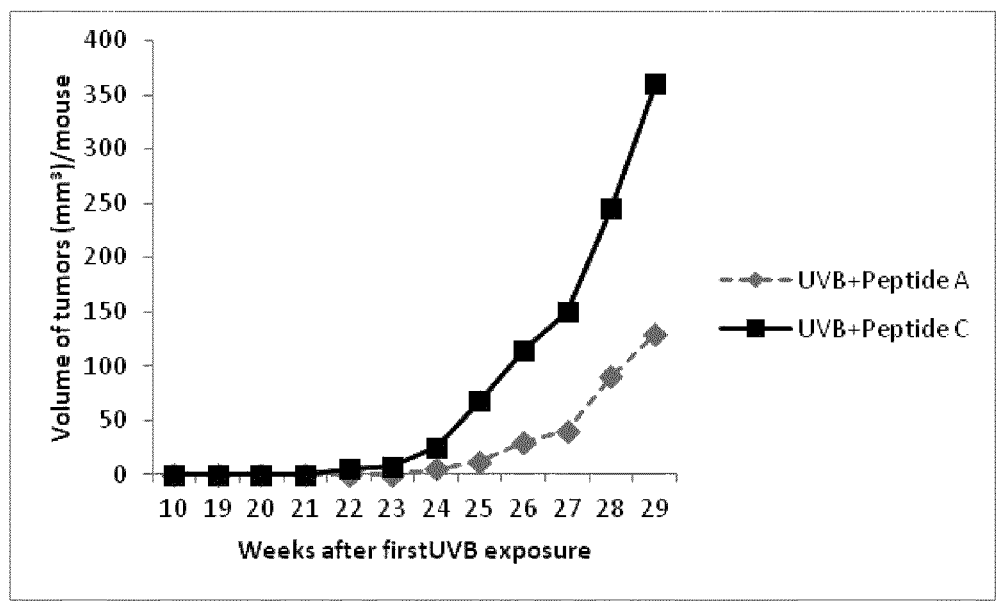
Figure 6C:
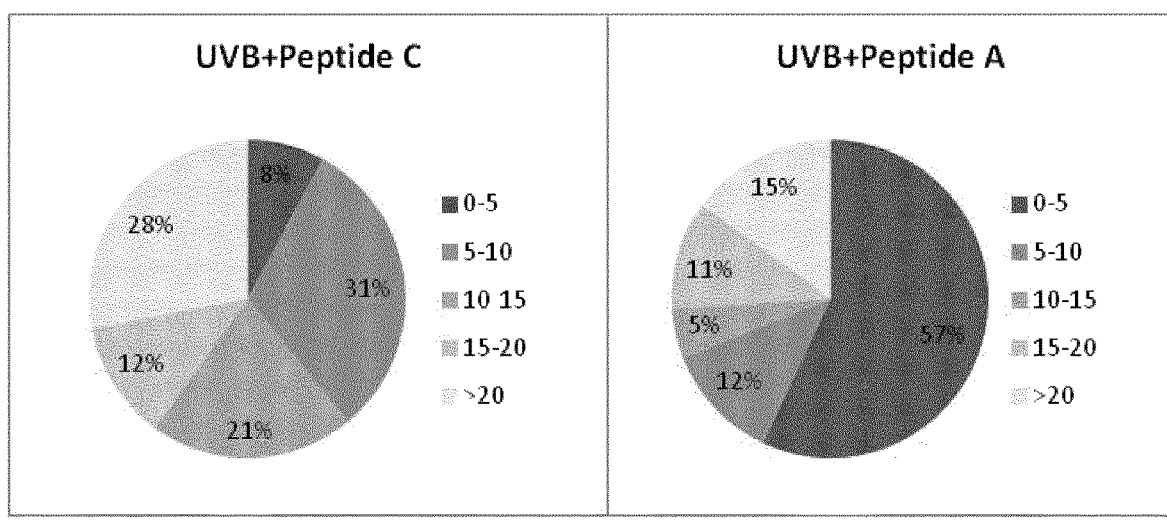

FIGS. 6A, 6B and 6C: show the photoprotective effects of peptide A on UVB-induced squamous cell carcinomas (SCC) induction using SKH-1 hairless mice. Mice were treated topically with 3 mg/kg of peptide A or control peptide, and irradiated with UVB 10 min later three times per week. The number (6A) and the size (6B) of tumors were assessed once a week during 29 weeks (6C). The tumor volume distribution was evaluated at week 29. Clearly there is a considerable reduction in numbers and size of UVB-induced tumors in SKH-1 mice administrated topically with peptide A.

Figure 7:
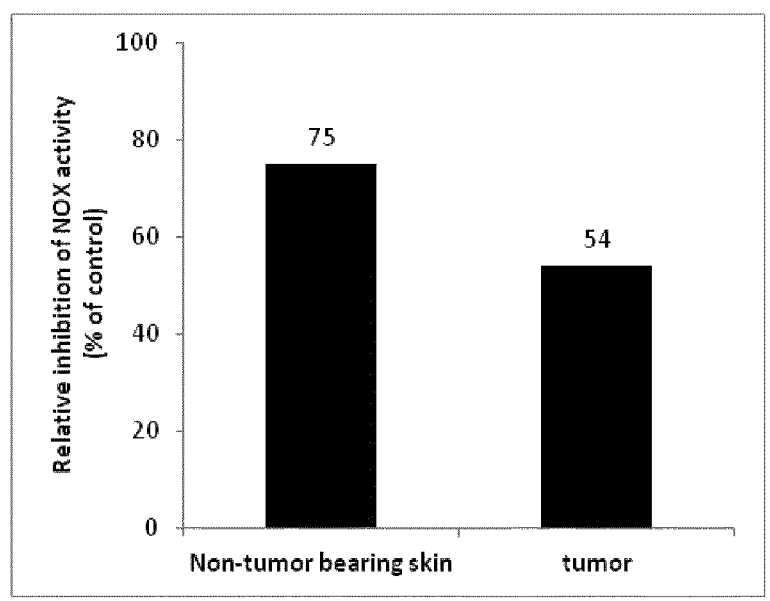

FIG. 7: shows a significant decrease in NADPH oxidase activity in both non-tumor bearing skin and UVB-induced tumors in SKH-1 mice treated with peptide A or control peptide. Mice were sacrificed after 29 weeks of treatment. Non-tumor bearing skin and tumors were harvested from irradiated mice treated with peptide A or the vehicle. NADPH oxidase activity was measured as RLU/µg of proteins in non-tumor bearing skin and UVB-induced tumors. Relative inhibition of Nox activity in non-tumor bearing skin and tumors was evaluated following arbitrary setting the Nox activity in non-tumor bearing skin and tumors taken from vehicle treated-mice to 100%. Results were then expressed as the average percentage of vehicle-treated mice.

Figures 8A, 8B:
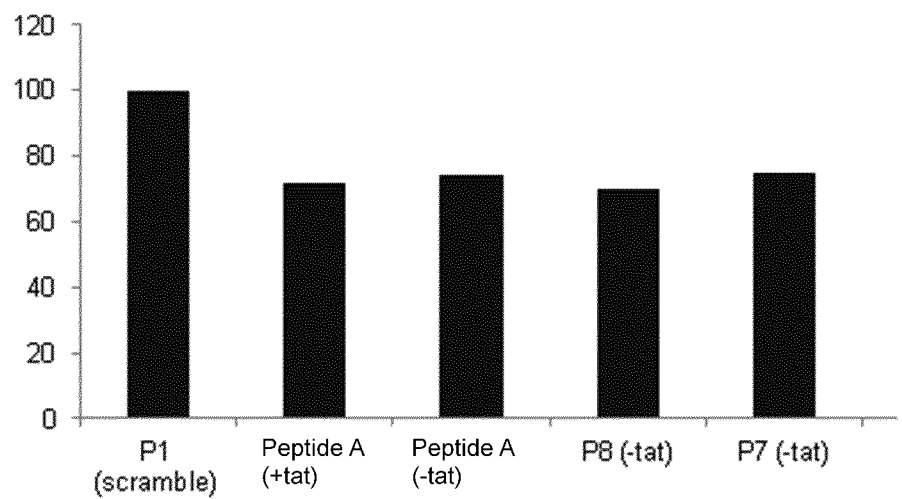

FIGS. 8A and 8B: show that the peptide A without tat can inhibit Nox activity as efficiently as peptide A. Moreover, the smaller peptides derived from peptide A efficiently inhibit the NADPH oxidase activity. Keratinocytes were treated with 10 µM of the indicated peptides: scramble control peptide P1 (SEQ ID NO: 57), peptide A with tat sequence (SEQ ID NO: 41) or without the tat sequence (SEQ ID NO:20); shorter peptides P7 (SEQ ID NO: 2) and P8 (SEQ ID NO: 56) (FIG. 8A). The NADPH oxidase activity was measured 24 h post-treatment (RLU/µg of proteins) and was normalized to the scramble treated cells (FIG. 8B).

Figure 9A:
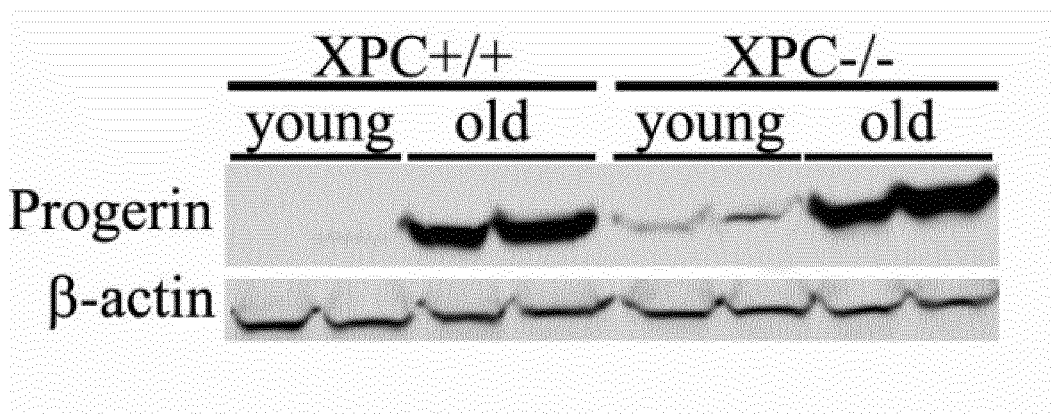
Figure 9B:
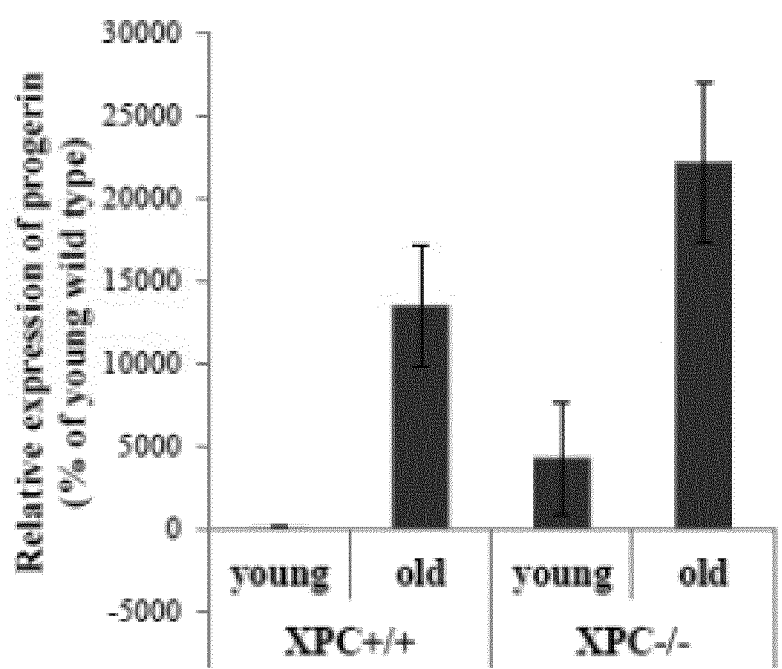

FIGS. 9A and 9B: show the progerin expression in skin biopsies of young and old XPC proficient (XPC$^{+/+}$) and deficient (XPC$^{-/-}$) mice. Young mice were 4 months old and old mice were 1.5 year old. (A) Total protein extracts of skin biopsies were assessed for progerin by Western blot analysis. β-actin was used as a loading control. (B) The protein bands corresponding to progerin was quantified and normalized with β-actin. The average density±SD from six mice in each group is presented as the relative value to the density in young wild type mice.

Figure 10A:
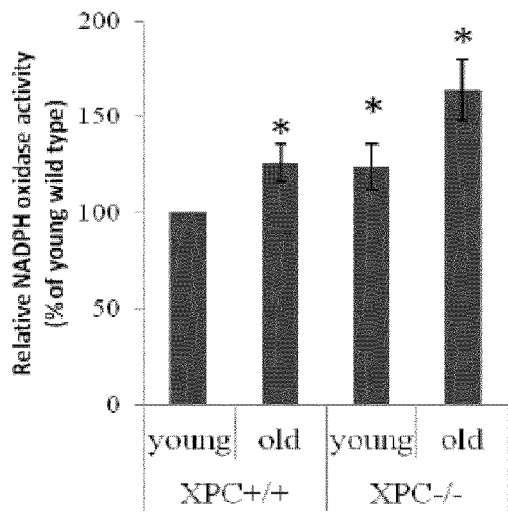
Figure 10B:
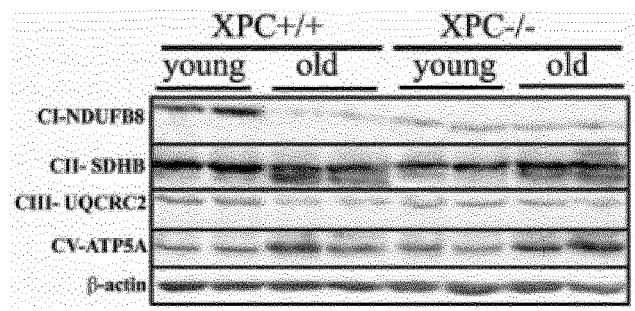
Figure 10C:
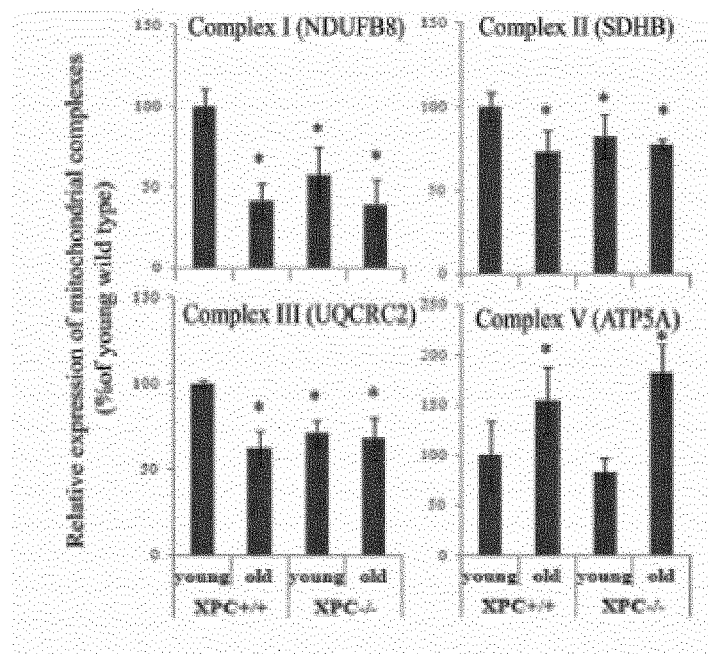

FIGS. 10A, 10B and 10C: show the effects of XPC deficiency on Nox activity and OXPHOS complexes expression. (A) NOX activity was measured (RLU/ug protein) in skin biopsies of young and old XPC$^{+/+}$ and XPC$^{-/-}$ mice. Results were normalized to the young wild type mice. (B) Expression of OXPHOS complexes were assessed by western blot analysis in young and old proficient and deficient XPC mice. (C) The bands corresponding to different OXPHOS complexes were quantified and normalized with β-actin. The average density±SD from six mice in each group is presented as the relative value to the density in young wild type mice.

Figure 11A:
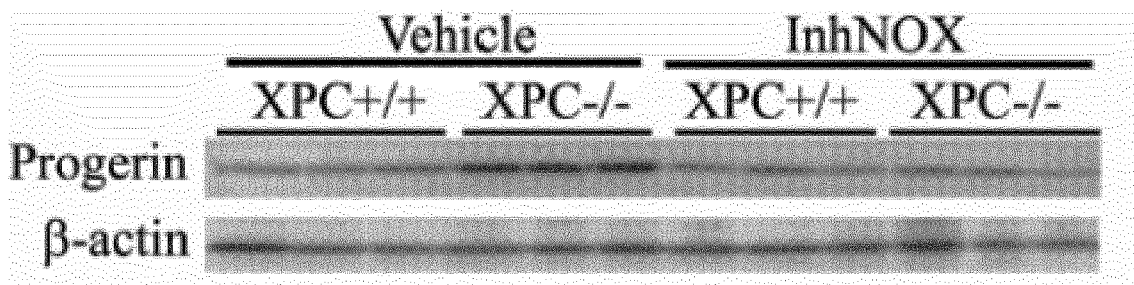
Figure 11B:
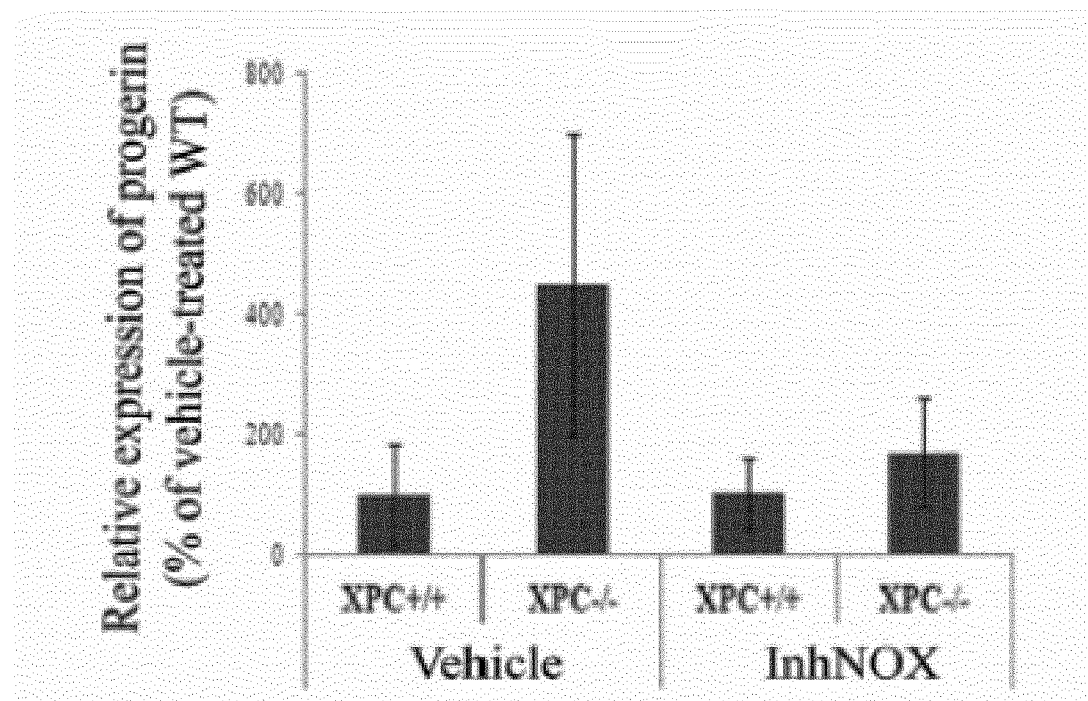

FIGS. 11A and 11B: show the effect of NOX1 inhibitor peptide A (InhNOX) on progerin expression in skin biopsies of young XPC$^{+/+}$ and XPC$^{-/-}$ mice. One month old mice were treated topically with 3 mg/kg (6 mice per group) Nox1 inhibitor peptide A (InhNOX) or control peptide (vehicle) three times per week for three months. (A) Total protein extracts of skin biopsies were assessed for progerin by Western blot analysis. β-actin was used as a loading control. (B) The protein bands corresponding to progerin was quantified and normalized with β-actin. The average density±SD from six mice in each group is presented as the relative value to the density in young wild type mice.

Figure 12A:
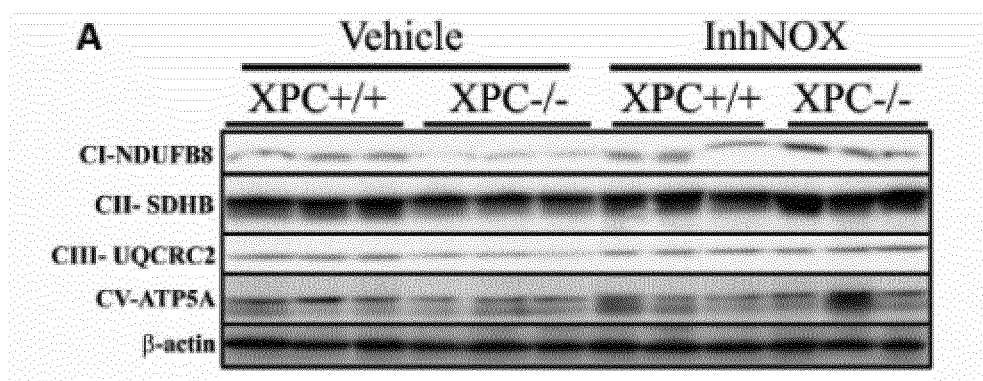
Figure 12B:
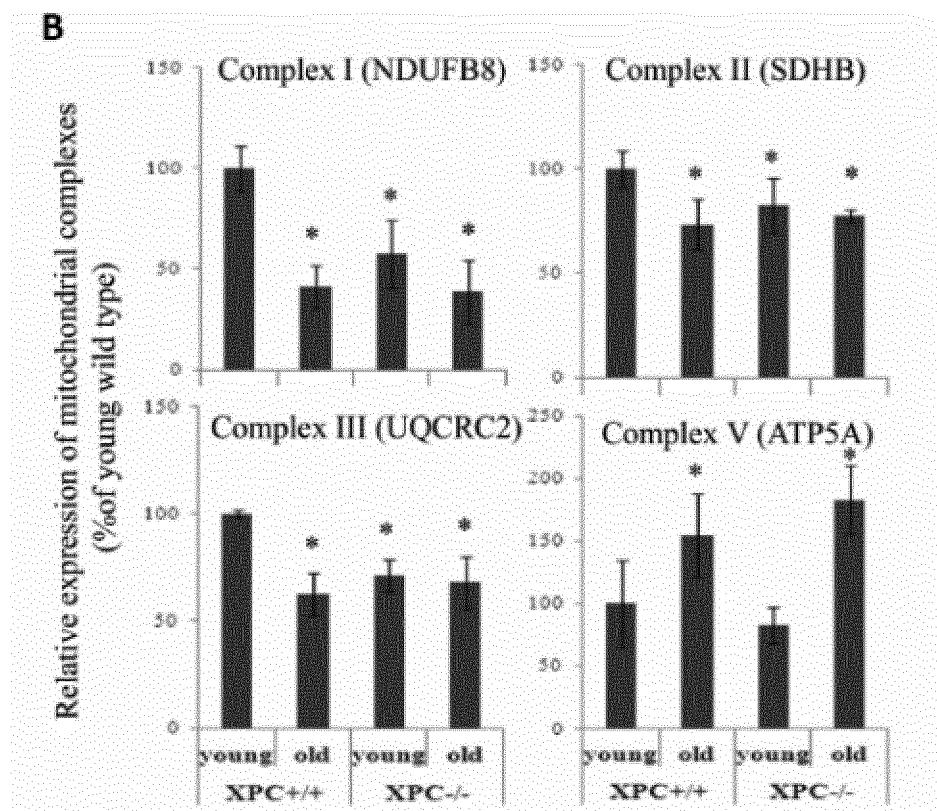

FIGS. 12A and 12B: show the effects of Nox1 inhibitor peptide A (InhNOX) on protein expression of OXPHOS complexes in skin biopsies of young XPC$^{+/+}$ and XPC$^{-/-}$ mice. One month old mice were treated topically with 3 mg/kg (6 mice per group) Nox1 inhibitor peptide A (InhNOX) or control peptide (vehicle) three times per week for three months. (A) Expression of OXPHOS complexes were assessed by western blot analysis. β-actin was used as a loading control. (B) The bands corresponding to different OXPHOS complexes were quantified and normalized with β-actin. The average density±SD from six mice in each group is presented as the relative value to the density in young wild type mice.

DETAILED DESCRIPTION

The present invention is directed towards novel selective peptides which are capable of selectively inhibiting Nox1 activation, by specifically blocking NADPH oxidase-1 assembly and consequently its activation, as well as their applications as medicament, and photoprotection agents. The invention thus relates to both therapeutic and cosmetic methods. These peptides may be designated hereinafter as Nox1 inhibitor peptides.

Additional modifications may entail peptide penetration into the cells for targeting proteins in the cytosol. An example of a successful method is adding an arginine rich sequence or a tat sequence. The peptides according to the present invention have been selected based on their potential abilities to compete with Nox1 assembly through interacting with Nox1.

The individuals who will be treated include humans and animals, preferably mammals, such as rodents and primates. The individual may be non-human animal or non-human mammal. The individual may have any of the conditions mentioned herein or may be at risk of developing them. In the case of human individuals they may be at least 50 years old, such as at least 60 or 70 years old.

The peptides of the invention derive from SEQ ID NO: 44 (the PRR region of NoxO1) or SEQ ID NO: 45 (the SH3 region of NoxA1). They will normally comprise 5 to 35 amino acids, or 5 to 20 amino acids, or 7 to 20 contiguous amino acids from SEQ ID NO:44 or SEQ ID NO:45. SEQ ID NO: 44 is PPTVPTRPSPGAIQSRCCTVTRRAL and SEQ ID NO: 45 is QVVAQHSYSAQGPEDLGFRQGDT-VDVLCEEPDVPLAVDQAWLEGHCDGRIGIFPKCFV-VPAGPRM.

The peptide of the invention typically comprises two distinct sequences. One of these is generally referred to as the 'portion' herein and this is responsible for the therapeutic activity of the peptide discussed herein. The portion may generally have a length of 5 to 20 amino acids, or 7 to 20 amino acids such as 7 to 19; 7 to 18; 7 to 17; 7 to 16; 7 to 15; 7 to 14; 7 to 13; 7 to 12; 7 to 11; 7 to 10; preferably 7 to 18; 7 to 15; 7 to 10; around 7 amino acids; or 8 to 18; 8 to 15; 8 to 10 amino acids.

The second distinct sequence, or any of the remainder of the sequence, within the peptide may provide additional advantageous properties to the peptide. This second part of the peptide may be absent, and so in one embodiment the peptide consists only of the 'portion' sequence described above which confers therapeutic properties, i.e., the length of the portion and peptide are the same. The second sequence is typically 0 to 31 amino acids in length, such as 5 to 30, 7 to 30, 10 to 25 or 15 to 20 amino acids in length. The second sequence may be a cell penetrating peptide, which is identical to or homologous with any of the specific cell penetrating peptides, mentioned herein. Clearly there may be additional 'second' sequence both at the N-terminal and C-terminal sides of the portion.

The peptide typically has a length of 7 to 35 amino acids, or 7 to 30, or 7 to 20, or 7 to 15, or 7 to 10, or around to 7, 8, 9 or 10 amino acids long, or preferably 7, 8, or 9, and most preferably 7 amino acids long.

The said peptide or portion may be, or may comprise a sequence as set forth in the general following amino acid general formula X1-P-X2-X3-P-X4-R (SEQ ID NO:1), wherein X1 is A, P or Q
X2 is P, T, V, A, S, C, M or K
X3 is L, I, V or A, and
X4 is T, V, S, A or M.

The said peptide or portion may be, or may also comprise, any of the sequences as listed in the Table 1 below or may be a homologue thereof:

TABLE 1

| PPTVPTR (SEQ ID NO: 2) |
| PPSVPTR (SEQ ID NO: 3) |
| PPMVPTR (SEQ ID NO: 4) |
| PPCVPTR (SEQ ID NO: 5) |
| PPPVPTR (SEQ ID NO: 6) |
| PPAVPTR (SEQ ID NO: 7) |
| PPVVPTR (SEQ ID NO: 8) |
| PPTVPSR (SEQ ID NO: 9) |
| PPTVPMR (SEQ ID NO: 10) |
| PPTVPVR (SEQ ID NO: 11) |

TABLE 1-continued

| PPTVPAR (SEQ ID NO: 12) |
| QPTAPTR (SEQ ID NO: 13) |
| PPTLPTR (SEQ ID NO: 14) |
| PPTIPTR (SEQ ID NO: 15) |
| PPTAPTR (SEQ ID NO: 16) |
| PPKVPTR (SEQ ID NO: 17) |
| QPTVPTR (SEQ ID NO: 18) |
| APTVPTR (SEQ ID NO: 19) |

According to another embodiment, the said peptide or portion may be, or may also comprise, any of the sequences as listed in the Tables 2 and 3 below or may be a homologue thereof:

TABLE 2

| PPTVPTRPS (SEQ ID NO: 20) |
| IQSRCCTVT (SEQ ID NO: 21) |
| PTVPTRP (SEQ ID NO: 22) |
| TVPTRPS (SEQ ID NO: 23) |
| RPSPGAI (SEQ ID NO: 24) |
| SPGAIQS (SEQ ID NO: 25) |
| PGAIQSR (SEQ ID NO: 26) |
| GAIQSRC (SEQ ID NO: 27) |
| AIQSRCC (SEQ ID NO: 28) |
| IQSRCCT (SEQ ID NO: 29) |
| QSRCCTV (SEQ ID NO: 30) |
| SRCCTVT (SEQ ID NO: 31) |

TABLE 3

| QVVAQHSYSA (SEQ ID NO: 32) |
| QGPEDLGFRQ (SEQ ID NO: 33) |
| LGFRQGDTVD (SEQ ID NO: 34) |
| GDTVDVLCEE (SEQ ID NO: 35) |
| VLCEEPDVPL (SEQ ID NO: 36) |
| PDVPLAVDQA (SEQ ID NO: 37) |
| AVDQAWLEGH (SEQ ID NO: 38) |

According to another embodiment, the present invention also provides a peptide or a portion comprising an amino acid sequence of at least 7 to 35 continuous amino acids, 7 to 30 continuous amino acids, or 7 to 20 continuous amino acids which may be identical to or have homology with a fragment of SEQ ID NO:44 (PRR region of NoxO1) or SEQ ID NO:45 (SH3 region of NoxA1). Suitable levels of homology are discussed in the section below relating to homology, and include for example analogues or conservative variants thereof. Preferably, the sequence of the therapeutic portion or peptide has 75%, 80%, 85%, 87%, 90%, 93%, 95%, 96%, 97%, 98%, or 99% identity to SEQ ID NO: 44 or SEQ ID NO: 45. Optionally said peptide is for use in a method of preventing and/or treating a pathological condition or disease associated either with Nox1 activity and/or increased reactive oxygen species (ROS) production. Preferably the said peptide is 7 to 15 amino acids long and/or said portion is preferably 7 to 10 amino acids long, more preferably around 7 amino acids long. Most preferably, the said peptide is identical to at least 7 contiguous amino acids of SEQ ID NO: 44 (PRR region of NoxO1) or SEQ ID NO: 45 (SH3 region of NoxA1), or has at least 80%, or 85%, or 90% or 95% identity to SEQ ID NO: 44 or SEQ ID NO: 45.

Homologous Sequences

Homologous sequences are mentioned herein. The homologous sequences may represent the therapeutic 'portion' sequence within the peptide or be the second (remainder) sequence in the peptide of the invention. The homologous sequences may be homologous of any of the specific sequences mentioned herein. A homologue has one or more (such as a least 2, 3, 4 or 5) additions and/or deletions and/or substitutions in comparison to the original sequence. The homologous sequence may comprise at least 70%, at least 75%, at least 80%, at least 85%, at least 87%, at least 90%, at least 95%, 96%, 97%, 98%, or at least 99% amino acid identity over the length of the original sequence or over 4, 6, 10, 15 or 20 amino acids of the original sequence.

The terms "sequence identity" typically refer to sequences which have the stated value when assessed using ClustalW (Thompson et al., 1994, supra) with the following parameters: Pairwise alignment parameters—Method: accurate, Matrix: PAM, Gap open penalty: 10.00, Gap extension penalty: 0.10; Multiple alignment parameters—Matrix: PAM, Gap open penalty: 10.00, % identity for delay: 30, Penalize end gaps: on, Gap separation distance: 0, Negative matrix: no, Gap extension penalty: 0.20, Residue-specific gap penalties: on, Hydrophilic gap penalties: on, Hydrophilic residues: G, P, S, N, D, Q, E, K. Sequence identity at a particular residue is intended to include identical residues which have simply been derivatized.

The homologous sequence may have 1, 2, 3, 4, 5 or more, or up to 10 amino acid substitutions in comparison to the original sequence. The substitutions are preferably conservative substitutions. These may be made according to the Table 4 below. Amino acids in the same block in the second column and preferably in the same line in the third column may be substituted for each other.

TABLE 4

| ALIPHATIC | Non-polar | G A P |
| | | I L V |
| | Polar-uncharged | C S T M |
| | | N Q |
| | Polar-charged | D E |
| | | K R |
| AROMATIC | | H F W Y |

The peptides of the present invention may be produced by any suitable method known in the art, such as chemical synthesis and/or recombinant DNA technology. For example, the inventive peptide can be synthesized using solid phase peptide synthesis techniques (e.g., Fmoc). Alternatively, the peptide can be synthesized using recombinant DNA technology (e.g., using bacterial or eukaryotic expression systems). A nucleotide sequence encoding a polypeptide of the invention may be constructed by isolating or synthesizing a nucleotide sequence encoding the parent peptide and then changing the nucleotide sequence so as to effect introduction (i.e. insertion or substitution) or removal (i.e. deletion or substitution) of the relevant amino acid residue(s). Methods for solid state protein synthesis and recombinant protein synthesis are well-known in the art. For example, "Molecular Cloning, A Laboratory Manual" (Sambrook et al., 3d Edition, Cold Spring Harmor Press), is a well-known reference detailing many suitable techniques for recombinant production of polypeptides. A variant of a peptide may be naturally occurring or it may be a variant that is not known to occur naturally. Non-naturally occurring variants of peptides may be made by direct synthesis, or alternatively, mutations can be introduced randomly along all or part of a peptide of this invention, such as by saturation mutagenesis or site-directed mutagenesis in accordance with conventional methods. Independent of the method of production, the resultant variants can be screened for the ability of Inhibiting Nox1 and/or ROS to identify variants of this invention.

The novel peptides can be isolated and/or purified (or substantially isolated and/or substantially purified). Accordingly, the invention provides the peptide of the first aspect of the present invention in isolated or substantially isolated form (e.g., substantially isolated from other peptides or impurities). The peptide can be isolated from other peptides as a result of solid phase protein synthesis, for example. Alternatively, the peptide can be substantially isolated from other proteins after cell lysis from recombinant production. Standard methods of protein purification (e.g., HPLC) can be employed to substantially purify the inventive peptides. Thus, a preparation of the peptide according to the present invention preferably is at least 90% (by weight) free of other peptides and/or contaminants, and more preferably is at least about 95% (by weight) free of other peptides and/or contaminants (such as at least about 97% or 98% (by weight) free of other peptides and/or contaminants).

The term "peptide" includes not only molecules in which amino acid residues are joined by peptide (—CO—NH—) linkages but also molecules in which the peptide bond is reversed. Such retro-inverso peptidomimetics may be made using methods known in the art. This approach involves making pseudopeptides containing changes involving the backbone, and not the orientation of side chains. Retro-inverse peptides, which contain NH—CO bonds instead of CO—NH peptide bonds, are much more resistant to proteolysis. Similarly, the peptide bond may be dispensed with altogether provided that an appropriate linker moiety which retains the spacing between the carbon atoms of the amino acid residues is used; it is particularly preferred if the linker moiety has substantially the same charge distribution and substantially the same planarity as a peptide bond. It will also be appreciated that the peptide may conveniently be blocked at its N- or C-terminus so as to help reduce susceptibility to exoproteolytic digestion. For example, the N-terminal amino group of the peptides may be protected by reacting with a carboxylic acid and the C-terminal carboxyl group of the peptide may be protected by reacting with an amine. Other examples of modifications include glycosylation and phosphorylation. Another potential modification is that hydrogens on the side chain amines of R or K may be replaced with methylene groups (—NH2-"—NH(Me) or —N(Me)2).

The peptide may be modified in other ways, for example to increase or decrease the peptide's half-life in vivo. Thus peptoid analogues, D-amino acid derivatives, and peptide-peptoid hybrids may be used. A further embodiment of the variant polypeptides used according to the invention comprises D-amino acid forms of the polypeptide. The preparation of polypeptides using D-amino acids rather than L-amino acids greatly decreases any unwanted breakdown of such an agent by normal metabolic processes, decreasing the amounts of agent which needs to be administered, along with the frequency of its administration.

The peptide of the invention is capable of reducing Nox1 activity, for example by at least 20%, or at least 30%, or at least 35%, 40%, 45%, 50%, 54%, 55%, 56%, 57%, 58%, 59%, or 60%. Preferably the peptide selectively decreases and/or inhibits Nox1 activity, but does not inhibit human NADPH oxidases selected among Nox2, Nox4, Nox5, Duox1, and Duox2. More preferably, the peptides according to the present invention selectively decrease and/or inhibit Nox1 activity through abrogating specifically the interaction between NoxO1 and NoxA1, but not p47phox and p67phox. The peptides according to the present invention as described herein above are thus Nox1 specific inhibitory peptides.

The present invention is further directed to methods and compositions for reducing NADPH oxidase or NOX induced ROS-mediated damage to a subject's skin or mucosal membranes. One embodiment of the present invention is a method for inhibiting and reducing NADPH oxidase or NOX induced ROS-mediated damage to a subject's skin or mucosal membranes comprising the step of delivering an effective dose of a peptide according to the present invention in a pharmaceutically acceptable carrier to a subject suffering from NADPH oxidase or NOX induced ROS-mediated damage to said subject's skin or mucosal membranes. Still further the present invention provides methods to modulate NADPH oxidase or NOX induced ROS-mediated free radicals responsible for oxidative tissue damage associated with pre-mature aging. The present invention further generally comprises incorporating peptides according to invention as a nutraceutical and/or pharmaceutical agent in suitable compositions. The term "modulate", "modulation" or "modulating" includes any increase or decrease in the activity of any component of NADPH oxidase or NOX system, specifically Nox1. As ROS are highly reactive molecules and can generate diverse damages in the cells, the ROS vicious cycle is believed to account for an exponential increase in oxidative damage during aging, which results in a gradually functional decline that characterizes the aging process.

In preferred embodiments the peptides and their compositions are very effective as photo-protecting agents. Sunlight has a profound effect on the skin causing premature skin aging, skin cancer, and a host of skin changes. Exposure to ultraviolet light, particularly UVA or UVB accounts for 90% of the symptoms of premature skin aging. Skin cancer is a serious consequence of chronic UV exposure. Ultraviolet (UV) radiation from the sun is the main cause of skin cancer. UV rays damage DNA, the genetic material that makes up genes. Genes control the growth and overall health of skin cells. If the genetic damage is severe, a normal skin cell may begin to grow in the uncontrolled, disorderly manner to become cancerous. UV also can cause sunburn, and other damage that makes the skin look prematurely old and wrinkled. There are different types of skin cancers depending on the type of skin cell from which they arise. Skin cancer can be a basal cell carcinoma, squamous cell carcinoma or malignant melanoma.

According to the present invention a composition based on peptides of the invention that enhances photoprotection to both UVA and UVB radiations is described. Such compositions can be used to treat subjects who are predisposed to the risks of skin damage associated with acute or chronic UV exposure. The said composition can be administered through topical, oral or intradermal means. The composition can easily be incorporated into topically applied vehicles such as solutions, suspensions, emulsions, oils, creams, ointments, powders, liniments, salves or the like, as a means of administering the active agents directly to a desired area of the skin. Further, the said composition may also be incorporated into oral dosage forms like capsules, tablets, syrups, toffees, chocolates, functional drinks and the like.

In preferred embodiments, the present invention provides a method directed to treating and/or preventing skin tumorigenesis following chronic UV exposition (UVA or UVB). In still further embodiments the present invention relates to a method of treating skin to provide protection from UV-radiation comprising: applying to the skin a composition comprising a therapeutically effective amount of the Nox1 inhibitor peptides as described above, or its analogues or conservative variants thereof wherein the peptide is optionally conjugated or attached to an agent which increases the accumulation of said peptide in a cell. Most preferably the peptide having a sequence according to the general amino acid formula of SEQ ID NO: 1 or in any of the amino acid sequences as set forth in SEQ ID NOs: 2 to 42, and preferably 2 to 19 may be used.

In still other preferred embodiments, the present invention is directed to a method for the treatment and/or care of skin, mucous membranes, scalp and/or hair which comprises administering a cosmetic or pharmaceutical effective amount of Nox1 inhibitor peptides as described above, analogues or conservative variants thereof wherein the peptide is optionally conjugated or attached to an agent which increases the accumulation of said peptide in a cell. Preferably, the peptide has the SEQ ID NO: 1 or 42. In preferred embodiments the invention is directed to method for the treatment and/or care for those conditions, disorders and/or pathologies of skin, mucous membranes, scalp and/or hair which are the result of the generation of ROS. Still specifically treatment and/or care afforded by the methods and compositions according to the present invention is photoprotection, protection of cell DNA and/or repair of cell DNA of skin, mucous membranes, scalp and/or hair.

According to alternate embodiments the treatment and/or skin care with the compositions of the present invention is done to reduce, postpone and/or prevent signs of aging, photoaging and the like. Specifically the disease conditions that may be treated can include skin conditions due to aging or premature aging wherein the peptide according to the invention is administered as an anti-aging agent or a photoprotectant.

The present invention also provides a composition that enhances photoprotection to both UVA and UVB induced skin damage, said composition comprising a therapeutically effective amount of a Nox1 inhibitor peptide as described above, analogues or conservative variants thereof. Said peptide may be optionally conjugated or attached to an agent, which increases the accumulation of said peptide in a cell. In preferred embodiments such a composition offers a safe, long-term therapeutic solution for subjects in need of enhanced photoprotection to both UVA and UVB rays. Specifically such a composition can be administered to subjects who are predisposed to the risks of skin cancer due to prolonged UVA and UVB exposure.

The present invention relates to a method of selectively reducing or inhibiting or modulating NOX/NADPH oxidase, specifically Nox1 activity, function or levels in a subject in need thereof. Said method comprises administering to the subject an effective amount of a Nox1 inhibitor peptide as described herein, wherein the peptide is optionally conjugated or attached to an agent which increases the accumulation of said peptide in a cell.

The present invention further provides a method of decreasing the levels of reactive oxygen species (ROS) or inhibiting production of reactive oxygen species (ROS), in a subject in need thereof, comprising administering to the subject an effective amount of a Nox1 inhibitor peptide as described herein, optionally conjugated or attached to an agent which increases the accumulation of said peptide in a cell.

The peptide is optionally conjugated or attached to an agent, which increases the accumulation of said peptide in a cell. Such conjugation with a suitable agent would render said peptide more membrane permeable, such as cell membrane permeable carriers. Such agent may be a cell membrane permeable carrier, for example a positively charged amino acid rich peptide, e.g., an arginine rich peptide. By way of example arginine rich peptide may be a polyarginine tag having the sequence RRRRRRRRR (SEQ ID NO: 46). Other cell penetrating peptides may be chosen among the NGR peptide derived from the aminopeptidase (CD13) N Ligand (CNGRCG: SEQ ID NO: 47), or Antennapedia Leader Peptide (CT) (KKWKMRRNQFWVKVQRG: SEQ ID: 48), Bcl-2 Binding Peptide (Decanoyl-KNL-WAAQRYGRELRRMSDEFEGSFKGL: SEQ ID NO: 49), a tat sequence (RKKRRQRRR: SEQ ID NO: 50), the buforin (TRSSRAGLQFPVGRVHRLLRK: SEQ ID NO: 51), a peptidic fragment of the Human T-cell Lymphotrophic Virus (HTLV)-II Rex (TRRQRTRRARRNR: SEQ ID NO: 52), the lipid membrane translocating peptide (KKAAAV-LLPVLLAAP: SEQ ID NO: 53), the NRP-1 Targeting Peptide, Streptomyces hygroscopicus (RPARPAR: SEQ ID NO: 54), and the penetratin (RQIKIWFQNRRMKWK-KGG: SEQ ID NO: 55).

The peptides according to the present invention can be used for prophylaxis and/or treatment of any NADPH oxidases-related disorder which may include cardiovascular diseases and disorders including, but is not limited to, hypertension, atherosclerosis, cardiac hypertrophy, heart failure, myocardial infarction, restenosis, diabetes, diabetic nephropathy, damage to intestinal mucosa (particularly to mucosal lesions of inflammatory bowel disease), neointimal hyperplasia and angina pectoris, other diseases and disorders coinciding with increased NADPH oxidases-mediated superoxide production including, but are not limited to, arthritis, chronic inflammatory bowel diseases (IBD), sepsis and other inflammatory disorders, bronchial asthma, chronic obstructive pulmonary disease (COPD), pulmonary infectious disease, lung fibrosis, Acute Respiratory Distress Syndrome (ARDS), cancer, auto-immune diseases, reperfusion injuries, kidney diseases, stroke, Alzheimer's disease, Parkinson's disease and other neurodegenerative diseases, cystic fibrosis, organ rejections, and pulmonary hypertension. Broadly peptides according to the invention can be used for prophylaxis or treatment of any reactive oxygen species (ROS) mediated inflammatory disorder including but not limited to, phosphorylation mediated disorders, polymorphonuclear leucocyte mediated disorders, macrophage mediated disorders, lipopolysaccharide mediated disorders, tumor necrosis factor-α mediated disorders, cytokine IFN-γ mediated disorders, interleukin-2 mediated disorders, inflammatory arthritis, potassium peroxochromate arthritis, rheumatoid arthritis, osteoarthritis or Alzheimer's disease. In preferred embodiments the present invention relates to a treatment or a prophylaxis, wherein the NADPH oxidase 1 (Nox1) activity or ROS activity leads to a disease condition selected from a group comprising of cardiovascular disorders, respiratory disorders, metabolism disorders, skin disorders, bone disorders, CNS disorders, neuro-inflammatory and/or neurodegenerative disorders, kidney diseases, sleep disorders, reproduction disorders, diseases affecting the eye and/or the lens, inflammatory disorders, liver diseases, pain, cancers, tumours Acute renal failure (ARF), allergic disorders, skin disorders, UV damage, skin conditions due to aging, photodamage of the skin, ROS induced skin damage, premature aging, age-related disease or disorder, disorders of the gastrointestinal system, angiogenesis disorders, atherosclerosis, restenosis after stent insertion, and/or hypertension and the like.

In a preferred embodiment the present invention provides a method of inhibiting tumor cell growth in a subject in need thereof comprising administering a therapeutically effective amount of a Nox1 inhibitor peptide according to the invention, analogues or conservative variants thereof. Said peptide may be optionally conjugated or attached to an agent which increases the accumulation of said peptide in a cell. In a most preferred embodiment the said inhibition of tumor cell growth is inhibition of tumorigenic keratinocyte growth. In yet another preferred embodiment the said is a method for treating and/or preventing skin tumorigenesis following chronic UV exposition (UVA or UVB).

In preferred aspects the methods according to the present invention are useful for a host of conditions selected from a group comprising of cancer, ROS induced skin damage, prevention of aging in skin and other age-related disorders, atherosclerosis, restenosis after stent insertion, and/or hypertension and the like. In very preferred embodiments the cancer that is amenable to treatment by the methods according to the present invention is selected from a group comprising of skin cancer, premalignant skin lesions, colon, colon adenocarcinomas, prostate cancers, benign or malignant papilloma and the like. The cancer may be melanoma or a hematopoietic malignancy, such as acute lymphoblastic leukemia (ALL), myelodysplastic syndrome (MDS), or a myeloid leukemia, such as chronic myeloid leukemia (CML) or acute myeloid leukemia (AML). It may be pancreatic cancer.

The cancer may be one caused by Ras-induced oncogenic cell transformation, such as colorectal cancer. The cancer may be adenocarcinoma or a *Helicobacter pylori* infection-induced gastrointestinal neoplasm. The cancer may be caused by papilloma virus. The cancer may be caused by xeroderma pigmentosum type C (XPC) gene silencing.

Broadly the present invention encompasses cosmetic or pharmaceutical composition comprising a cosmetically or pharmaceutically or therapeutically effective amount of at least one peptide of the invention or mixtures of peptides or the invention with a pharmaceutically acceptable salt, and typically at least one cosmetically or pharmaceutically acceptable excipient or adjuvant.

The present invention also provides pharmaceutical or nutraceutical compositions for inhibiting or modulating Nox1 activity in a subject, comprising a peptide of the invention. In still other preferred embodiments the present invention provides compositions for selectively reducing and/or inhibiting Nox1 activity in a subject in need thereof, or compositions for decreasing the levels of reactive oxygen species (ROS) or inhibiting production of reactive oxygen species (ROS) in a subject in need thereof, wherein the said composition comprises an efficient amount of a Nox1 inhibitor peptide according to the present invention. In a most preferred embodiment the present invention provides a composition for selectively reducing and/or inhibiting Nox1 activity and or decreasing the levels of reactive oxygen species (ROS) or inhibiting production of reactive oxygen species (ROS) in a subject in need thereof, comprising an effective amount of a peptide having an amino acid sequence selected among SEQ ID NO:1 to 42 and preferably 1 to 19 analogues or conservative variants thereof, wherein the peptide is optionally conjugated or attached to an agent which increases the accumulation of said peptide in a cell.

In still another aspect, the present invention relates to compositions comprising peptides according to the present invention wherein said composition further comprising a pharmaceutically acceptable excipient or carrier. Specifically, the present invention relates to the use of the Nox1 inhibitor peptides of the present invention as an active ingredient, together with at least one pharmaceutically acceptable carrier, excipient and/or diluents for the manufacture of a pharmaceutical composition for the treatment and/or prophylaxis diseases disclosed herein. Such pharmaceutical compositions comprise the Nox1 inhibitor peptide together with at least one pharmaceutically acceptable carrier, excipient, binders, disintegrates, glidents, diluents, lubricants, colouring agents, sweetening agents, flavouring agents, preservatives or the like. The pharmaceutical compositions of the present invention can be prepared in a conventional solid or liquid carrier or diluents and a conventional pharmaceutically-made adjuvant at suitable dosage level in a known way. Administration forms include, for example, pills, tablets, film tablets, coated tablets, capsules, liposomal formulations, micro- and nano-formulations, powders and deposits. Furthermore, the present invention also includes pharmaceutical preparations for parenteral application, including dermal, intradermal, intragastral, intracutaneous, intravasal, intravenous, intramuscular, intraperitoneal, intranasal, intravaginal, intrabuccal, percutaneous, rectal, subcutaneous, sublingual, topical, or transdermal application, which preparations in addition to typical vehicles and/or diluents containing the novel peptides according to the present invention. Techniques for the formulation and administration of the peptide of the present invention may be found in "Remington's Pharmaceutical Sciences" Mack Publishing Co., Easton Pa.

The peptides of the invention can also be administered in form of its pharmaceutically active salts. Suitable pharmaceutically active salts comprise acid addition salts and alkali or earth alkali salts. For instance, sodium, potassium, lithium, magnesium or calcium salts can be obtained. The Nox1 inhibitor peptide or peptide combination of the present invention forms pharmaceutically acceptable salts with organic and inorganic acids. Examples of suitable acids for such acid addition salt formation are hydrochloric acid, hydrobromic acid, sulfuric acid, phosphoric acid, acetic acid, citric acid, oxalic acid, malonic acid, salicylic acid, p-aminosalicylic acid, malic acid, fumaric acid, succinic acid, ascorbic acid, maleic acid, sulfonic acid, phosphonic acid, perchloric acid, nitric acid, formic acid, propionic acid, gluconic acid, lactic acid, tartaric acid, hydroxymaleic acid, pyruvic acid, phenylacetic acid, benzoic acid, p-aminobenzoic acid, p-hydroxybenzoic acid, methanesulfonic acid, ethanesulfonic acid, nitrous acid, hydroxyethanesulfonic acid, ethylenesulfonic acid, p-toluenesulfonic acid, naphthylsulfonic acid, sulfanilic acid, camphersulfonic acid, china acid, mandelic acid, o-methylmandelic acid, hydrogen-benzenesulfonic acid, picric acid, adipic acid, D-o-tolyl tartaric acid, tartronic acid, α-toluic acid, (o, m, p)-toluic acid, naphthylamine sulfonic acid, and other mineral or carboxylic acids well known to those skilled in the art. The salts are prepared by contacting the free base form with a sufficient amount of the desired acid to produce a salt in the conventional manner.

In one embodiment of this aspect of the invention, the Nox1 inhibitor peptide of the present invention may be conjugated to a non-peptide moiety. A polymer molecule to be coupled to the peptide may be any suitable polymer molecule, such as a natural or synthetic homo-polymer or hetero-polymer, typically with a molecular weight in the range of about 300-100,000 Da, such as about 500-20,000 Da. Examples of suitable polymer molecules include polymer molecules selected from the group consisting of polyalkylene oxide (PAO), including polyalkylene glycol (PAG), such as polyethylene glycol (PEG) and polypropylene glycol (PPG), branched PEGs, poly-vinyl alcohol (PVA), polycarboxylate, poly-(vinylpyrolidone), polyethylene-co-maleic acid anhydride, polystyrene-co-maleic acid anhydride, dextran, including carboxymethyl-dextran, or any other biopolymer suitable for reducing immunogenicity and/or increasing functional in vivo half-life and/or serum half-life. Another example of a polymer molecule is human albumin or another abundant plasma protein. Generally, polyalkylene glycol-derived polymers are biocompatible, non-toxic, non-antigenic, non-immunogenic, have various water solubility properties, and are easily excreted from living organisms.

The Nox1 inhibitor peptides of the present invention can also be incorporated into pharmaceutical delivery systems and/or sustained release systems, the term "delivery systems" relates to a diluent, adjuvant, excipient or carrier with which the peptide of the invention is administered. These cosmetic or pharmaceutical carriers can be liquids, such as water, oils or surfactants, including those of petroleum, animal, vegetable or synthetic origin, such as and not restricted to, peanut oil, soybean oil, mineral oil, sesame oil, castor oil, polysorbates, sorbitan esters, ether sulfates, sulfates, betaines, glycosides, maltosides, fatty alcohols, nonoxynols, poloxamers, polyoxyethylcnes, polyethylene glycols, dextrose, glycerol, digitonin and similar. In "Remington's Pharmaceutical Sciences" by E. W. Martin diluents, adjuvants or excipients are described as appropriate carriers. The term "sustained release" is used in a conventional sense relating to a delivery system of a compound which provides the gradual release of this compound during a period of time and preferably, although not necessarily, with relatively constant compound release levels over a period of time. Examples of delivery or sustained release systems are liposomes, mixed liposomes, oleosomes, niosomes, ethosomes, milliparticles, microparticles, nanoparticles and solid lipid nanoparticles, nanostructured lipid carriers, sponges, cyclodextrins, vesicles, micelles, mixed micelles of surfactants, surfactant-phospholipid mixed micelles, millispheres, microspheres and nanospheres, lipospheres, millicapsules, microcapsules and nanocapsules, as well as micro-emulsions and nano-emulsions, which can be added to achieve a greater penetration of the Nox1 inhibitor peptides and/or improve its pharmacokinetic and pharmacodynamic properties. Preferred delivery or sustained release systems are liposomes, surfactant-phospholipid mixed micelles and micro-emulsions, more preferably water-in-oil micro-emulsions with an internal structure of reverse micelle.

When used as a photoprotectant or anti-aging agent, the compositions of the invention may also comprise conventional cosmetic additives and adjuvants selected, in particular, from fatty substances, organic solvents, thickeners, softeners, antioxidants, opacifying agents, stabilizers, emollients, hydroxy acids, antifoaming agents, moisturizers, vitamins, fragrances, preservatives, surfactants, fillers, sequestering agents, polymers, propellants, basifying or acidifying agents, dyes, colorants, or any other ingredient usually formulated into cosmetics, in particular for the manufacture of antisun/sunscreen compositions in the form of emulsions.

The methods and compositions of the present invention can be used in combination with other compositions and procedures for the treatment of diseases. For example, a tumor can be treated conventionally with surgery, radiation, chemotherapy, or immunotherapy, combined with methods and compositions of the present invention. The methods and compositions of the present invention can then also be subsequently administered to the patient to extend the dormancy of micrometastases and to stabilize and inhibit the growth of any residual primary tumor. The compositions of the present invention may also be combined with other anti-angiogenic compounds, or proteins, fragments, antisera, receptor agonists, receptor antagonists of other anti-angiogenic proteins. Additionally the novel Nox1 inhibitor peptides of the present invention can be combined with pharmaceutically acceptable excipients, and optionally sustained-release matrix, such as biodegradable polymers, to form therapeutic compositions.

Additionally, compositions of the present invention may be administered concurrently with other therapies, e.g., in conjunction with a chemotherapy or radiation therapy regimen. Examples of chemotherapeutic agents that can be combined with the novel Nox1 inhibitor peptides according to the present invention include alkylating agents, for example, nitrogen mustards, ethyleneimine compounds, alkyl sulphonates and other compounds with an alkylating action such as nitrosoureas, cisplatin and dacarbazine; antimetabolites, for example, folic acid, purine or pyrimidine antagonists; mitotic inhibitors, for example, vinca alkaloids and derivatives of podophyllotoxin; cytotoxic antibiotics and camptothecin derivatives. Preferred chemotherapeutic agents or chemotherapy include amifostine (ethyol), cisplatin and/or other platinum compounds, preferably including carboplatin and/or oxaliplatin, dacarbazine (DTIC), dactinomycin, mechlorethamine (nitrogen mustard), streptozocin, cyclophosphamide, carmustine (BCNU), lomustine (CCNU), doxorubicin (adriamycin), doxorubicin lipo (doxil), gemcitabine (gemzar), daunorubicin, daunorubicin lipo (daunoxome), procarbazine, mitomycin, cytarabine, etoposide, methotrexate, 5-fluorouracil (5-FU), vinblastine, vincristine, bleomycin, paclitaxel (taxol), docetaxel (taxotere), aldesleukin, asparaginase, busulfan, carboplatin, cladribine, camptothecin, CPT-1 1, 10-hydroxy-7-ethyl-camptothecin (SN38), dacarbazine, floxuridine, fludarabine, hydroxyurea, ifosfamide, idarubicin, mesna, interferon alpha, interferon beta, irinotecan, mitoxantrone, topotecan, leuprolide, megestrol, melphalan, mercaptopurine, plicamycin, mitotane, pegaspargase, pentostatin, pipobroman, plicamycin, streptozocin, tamoxifen, teniposide, testolactone, thioguanine, thiotepa, uracil mustard, vinorelbine, chlorambucil, and combinations thereof.

When used for treatment or management of atherosclerosis, restenosis after stent insertion, and/or hypertension, the Nox1 inhibitor peptides according to the present invention may either be used alone or in combination with other drugs used for treatment and/or management of atherosclerosis, restenosis after stent insertion, and/or hypertension. Such other drugs may include but are not restricted to thrombolytic agents such as streptokinase, tissue plasminogen activator, plasmin and urokinase, anti-thrombotic agents such as tissue factor protease inhibitors (TFPI), nematode-extracted anticoagulant proteins (NAPs) and the like, metalloproteinase inhibitors, anti-inflammatory agents, antidiabetic or antihyperglycemic agents including insulin, insulin secretagogues, or insulin sensitizers, SGLT-2 inhibitors, $AT_1$-receptor antagonist, a HMG-Co-A reductase inhibitor, an angiotensin converting enzyme (ACE) inhibitor, an calcium channel blocker, an aldosterone synthase inhibitor, an aldosterone antagonist, an dual angiotensin converting enzyme/neutral endopetidase (ACE/NEP) inhibitor, an endothelin antagonist, a diuretic and the like.

When used as an anti-aging agent or a photoprotectant, the Nox1 inhibitor peptides of the present invention may be combined with one or more of botanicals/plant extracts; thiodipropionic acid (TDPA) and esters thereof; retinoids (e.g., all-trans retinoic acid, 9-cis retinoic acid, phytanic acid and others); hydroxy acids (including alpha-hydroxyacids and beta-hydroxyacids), salicylic acid and salicylates; exfoliating agents (e.g., glycolic acid, 3,6,9-trioxaundecanedioic acid, etc . . . ), estrogen synthetase stimulating compounds (e.g., caffeine and derivatives); compounds capable of inhibiting 5 alpha-reductase activity (e.g., linolenic acid, linoleic acid, finasteride, and mixtures thereof); barrier function enhancing agents (e.g., ceramides, glycerides, cholesterol and its esters, alpha-hydroxy and omega-hydroxy fatty acids and esters thereof, etc . . . ); collagenase inhibitors; and elastase inhibitors and the like.

The anti-aging or photoprotectant compositions may also include one or more of the following: a skin penetration enhancer, an emollient, a skin plumper, an optical diffuser, a sunscreen, an exfoliating agent, and an antioxidant. An emollient provides the functional benefits of enhancing skin smoothness and reducing the appearance of fine lines and coarse wrinkles. These include by way of examples, isopropyl myristate, petrolatum, isopropyl lanolate, silicones (e.g., methicone, dimethicone), oils, mineral oils, fatty acid esters, or any mixtures thereof. The emollient may be preferably present from about 0.1 wt % to about 50 wt % of the total weight of the composition.

A skin plumper serves as a collagen enhancer to the skin. An example of a suitable, and preferred, skin plumper is palmitoyl oligopeptide. Other skin plumpers are collagen and/or other glycosaminoglycan (GAG) enhancing agents. When present, the skin plumper may comprise from about 0.1 wt % to about 20 wt % of the total weight of the composition. An optical diffuser is a particle that changes the surface optometrics of skin, resulting in a visual blurring and softening of, for example, lines and wrinkles. Examples of optical diffusers that can be used in the present invention include, but are not limited to, boron nitride, mica, nylon, polymethylmethacrylate (PMMA), polyurethane powder, sericite, silica, silicone powder, talc, Teflon, titanium dioxide, zinc oxide, or any mixtures thereof. When present, the optical diffuser may be present from about 0.01 wt % to about 20 wt % of the total weight of the composition.

A sunscreen for protecting the skin from damaging ultraviolet rays may also be included. Preferred sunscreens are those with a broad range of UVB and UVA protection, such as octocrylene, avobenzone (Parsol 1789), octyl methoxycinnamate, octyl salicylate, oxybenzone, homosylate, benzophenone, camphor derivatives, zinc oxide, and titanium dioxide. When present, the sunscreen may comprise from about 0.01 wt % to about 70 wt % of the composition.

Suitable exfoliating agents include, for example, alpha-hydroxyacids, beta-hydroxyacids, oxaacids, oxadiacids, and their derivatives such as esters, anhydrides and salts thereof. Suitable hydroxy acids include inter alia glycolic acid, lactic acid, malic acid, tartaric acid, citric acid, 2-hydroxyalkanoic acid, mandelic acid, salicylic acid and derivatives thereof. A preferred exfoliating agent is glycolic acid. When present, the exfoliating agent may comprise from about 0.1 wt % to about 80 wt % of the composition.

An antioxidant functions, among other things, to scavenge free radicals from skin to protect the skin from environmental aggressors. Examples of antioxidants that may be used in the present compositions include compounds having phenolic hydroxy functions, such as ascorbic acid and its derivatives/esters; beta-carotene; catechins; curcumin; ferulic acid derivatives ethyl ferulate, sodium ferulate); gallic acid derivatives (e.g., propyl gallate); lycopene; reductic acid; rosmarinic acid; tannic acid; tetrahydrocurcumin; tocopherol and its derivatives; uric acid; or any mixtures thereof. Other suitable antioxidants are those that have one or more thiol functions (—SH), in either reduced or non-reduced form, such as glutathione, lipoic acid, thioglycolic acid, and other sulfhydryl compounds. The antioxidant may be inorganic, such as bisulfites, metabisulfites, sulfites, or other inorganic salts and acids containing sulfur.

Other conventional additives include vitamins, such as tocopherol and ascorbic acid; vitamin derivatives such as ascorbyl monopalmitate; thickeners such as hydroxyalkyl cellulose; gelling agents; structuring agents such as bentonite, smectite, magnesium aluminum silicate and lithium magnesium silicate; metal chelating agents such as EDTA; pigments such as zinc oxide and titanium dioxide; colorants; emollients; and humectants.

The present invention also extends to a portion or part or fragment of the Nox 1 gene or its mRNA, specifically NADPH oxidase 1 isoform long variant, NADPH oxidase activator 1 isoform 3, NADPH oxidase organizer 1 isoform. Particularly the present invention relates to nucleic acid sequences encoding the peptides according to the present invention. A "portion or part or fragment" is defined as having a minimal size of at least about 8 nucleotides or preferably about 12-17 nucleotides or more preferably at least about 18-25 nucleotides and may have a maximal size of at least about 5000 nucleotides. Genomic equivalents larger than 5000 nucleotides may also be employed. This definition includes all sizes in the range of 8-5000 nucleotides. Thus, this definition includes nucleic acids of at least 12, 15, 20, 25, 40, 60, 80, 100, 200, 300, 400, 500 or 1000 nucleotides or nucleic acids having any number of nucleotides within these values (e.g., 13, 16, 23, 30, 28, 50, 72, 121 nucleotides, etc. . . . ) or nucleic acids having more than 500 nucleotides or any number of nucleotides between 500. The present invention includes all novel nucleic acids having at least 8 nucleotides derived from nucleic acids encoding the Nox1 inhibitor peptides according to the present invention, the complement or a functional equivalent thereof. In the most preferred embodiment the present invention provides a nucleic acid encoding peptide of SEQ ID NO: 2 to 42 analogues or conservative variants thereof. Still further the invention pertains to plasmids or vectors comprising the nucleic acids encoding the Nox1 inhibitor peptides of the present invention. The nucleic acids, plasmids and vectors of the invention may be used to treat any of the conditions mentioned herein.

The peptide according to the present invention may be labelled with one or more detectable labels. The label may be conjugated to the peptide either directly or by use of a linker. When the peptide according to the present invention is conjugated to a direct label, the direct label is suitably an entity which is detectable in its natural state. For example, where the direct label is a coloured particle, such as dye sols, metallic sols (e.g. colloidal gold), and coloured latex particles, this may be visible to the naked eye, or become visible with the aid of an optical filter. Where the direct label is a fluorescent label, this may be subjected to applied stimulation, e.g., UV light to promote fluorescence. Suitable detectable substances include various enzymes, prosthetic groups, fluorescent materials, luminescent materials and radioactive materials.

In one embodiment of the invention, the Nox1 inhibitor peptides according to the invention may be conjugated to one or more detection, diagnostic or therapeutic agent for selective delivery to disease sites such as cancer cells, particularly in humans. The conjugation may be either directly or by use of a linker, analogously to the conjugation described above. The corresponding methods of detection, diagnosis and therapy of the diseases are corresponding aspects of the present invention, as are the peptides for use in such detection, diagnosis and therapeutic methods. Detection, diagnostic and therapeutic agents may be naturally-occurring, modified, or synthetic. Therapeutic agents may promote or inhibit any biological process implicated in a human disease pathway. The methods of detection, diagnosis and therapy, using the peptides according to the present invention conjugated to one or more detection, diagnostic or therapeutic agent for selective delivery to disease sites, may be performed in vitro, particularly on a sample obtained from a subject, or in vivo in the body of a subject (patient) to be tested or treated. For example, the additional agent can be a therapeutic agent art-recognized as being useful to treat cancer. The specific binding interaction between the peptide and the cells enables the therapeutic agent to be accurately targeted to cancerous cells in a mammalian patient. Therapeutic agents suitable for this use may include any compound that induces apoptosis, cell death, cell differentiation, cell stasis and/or anti-angiogenesis or otherwise affects the survival and/or growth rate of a cancer cell.

The invention further provides a method of preparing the Nox1 inhibitor peptide of the invention by solid phase or liquid phase synthesis, wherein said method optionally comprises a step of conjugating or attaching an agent which increase the accumulation of said peptide in a cell.

Delivery Methods

Once formulated the compositions of the invention (containing the peptide or polynucleotide of the invention) can be delivered to a subject in vivo using a variety of known routes and techniques. For example, a composition can be provided as an injectable solution, suspension or emulsion and administered via parenteral, subcutaneous, epidermal, intradermal, intramuscular, intra-arterial, intraperitoneal, intravenous injection using a conventional needle and syringe, or using a liquid jet injection system. Compositions can also be administered topically to skin or mucosal tissue, such as nasally, intratracheally, intestinally, rectally or vaginally, or provided as a finely divided spray suitable for respiratory or pulmonary administration. Other modes of administration include oral administration, suppositories, sublingual administration, and active or passive transdermal delivery techniques.

Delivery Regimes

Administration of the peptides/polynucleotides may be by any suitable method as described above. Suitable amounts of the peptide may be determined empirically, but typically are in the range given below. A single administration of each peptide may be sufficient to have a beneficial effect for the patient, but it will be appreciated that it may be beneficial if the peptide is administered more than once, in which case typical administration regimes may be, for example, once or twice a week for 2-4 weeks every six months, or once a day for a week every four to six months. As will be appreciated, each peptide or polynucleotide, or combination of peptides and/or polynucleotides may be administered to a patient singly or in combination.

Dosages for administration will depend upon a number of factors including the nature of the composition, the route of administration and the schedule and timing of the administration regime. Suitable doses of a molecule or a combination of molecules of the invention may be in the order of 1 µg up to 10 µg, up to 15 µg, up to 20 µg, up to 25 µg, up to 30 µg, up to 35 µg, up to 50 µg, up to 100 µg, up to 500 µg or more per administration. Suitable doses may be less than 15 µg, but at least 1 ng, or at least 2 ng, or at least 5 ng, or at least 50 ng, or least 100 ng, or at least 500 ng, or at least 1 µg, or at least 10 µg. For some molecules of the invention, the dose used may be higher, for example, up to 1 mg, up to 2 mg, up to 3 mg, up to 4 mg, up to 5 mg or higher. Such doses may be provided in a liquid formulation, at a concentration suitable to allow an appropriate volume for administration by the selected route.

EXAMPLES

Two further peptides named A and B according to the present invention have been tested and compared with a control peptide C as listed in Table 5 below.

Peptide A (SEQ ID NO:41) comprises a tat sequence which is N-terminal to the sequence SEQ ID NO:20. Peptide B (SEQ ID NO:42) comprise a tat sequence which is N-terminal to the sequence SEQ ID NO:21. Peptide C (SEQ ID NO:43) is a control peptide (or scramble peptide).

TABLE 5

Target and sequences of inhibiting peptides

| Peptides | Target of peptides | Sequences |
|---|---|---|
| A | SH3-NoxA1 | tat-P-P-T-V-P-T-R-P-S (SEQ ID No: 41) |
| B | SH3-NoxA1 | tat-I-Q-S-R-C-C-T-V-T (SEQ ID No: 42) |
| C | Scramble | tat-C-L-R-I-T-R-Q-S-R (SEQ ID No: 43) |

Figure 1A:
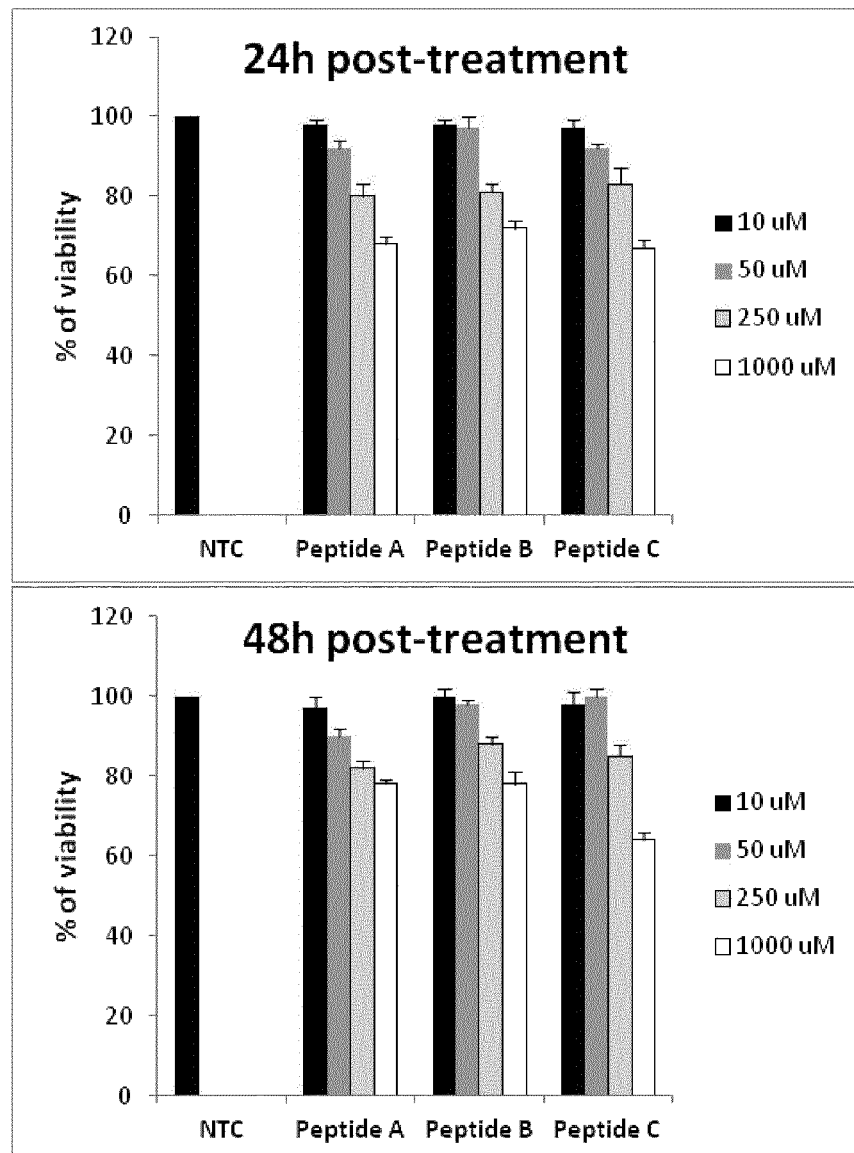
FIGS. 1A and 1B: show the cytotoxic effect of each peptide tested on normal primary human keratinocytes using trypan blue exclusion assay and MTT assay.
Figure 1B:
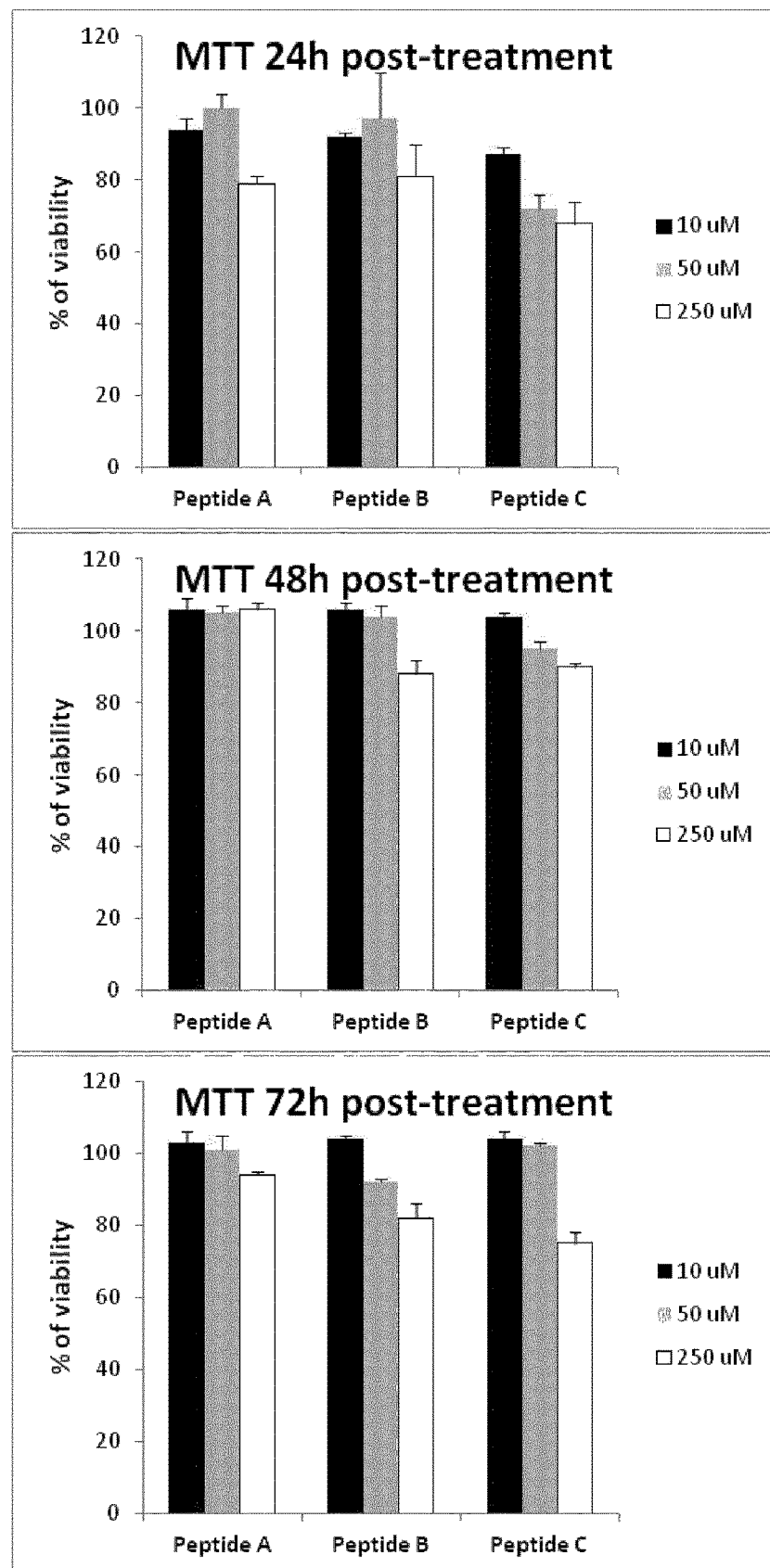

The cytotoxic effect of each peptide was first tested on normal primary human keratinocytes using trypan blue exclusion assay and MTT assay. As illustrated in FIGS. 1A and 1B, no significant toxicity was observed after treatment with less than 50 µM of peptides.

Nox1 inhibitor peptides were found to efficiently diminish intracellular ROS levels as demonstrated by the following results.

Figure 2A:
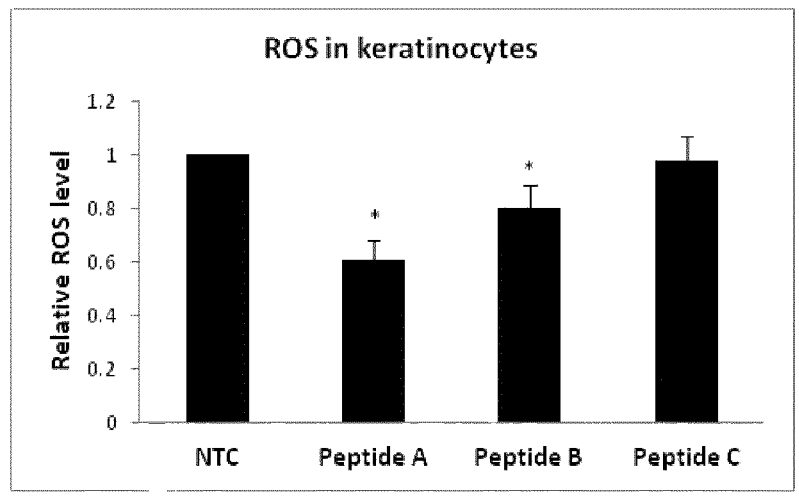
FIGS. 2A and 2B: show the relative ROS level as measured in primary human keratinocytes and HT29 (human colon adenocarcinoma cell line) treated with 10 or 50 µM of peptide inhibitor for 24 h using the CM-H2DCF-DA probes. Cells were treated with 10 µM of the peptides A (SEQ ID NO: 41), B (SEQ ID NO: 42), and C (SEQ ID NO: 43), and the ROS level was measured 24 h post-treatment. ROS level was normalized to non-treated cells (NTC) (*P<0.05). As per FIG. 2A, a significant decrease in ROS level was observed in keratinocytes cells treated with peptide A (SEQ ID NO: 41) and peptide B (SEQ ID NO: 42). As per FIG. 2B measurement of ROS level in HT29 cells showed that treatment with peptides A and B resulted in a significant reduction in ROS level, suggesting a specific inhibitory effect of these peptides on Nox1 activity.
Figure 2B:
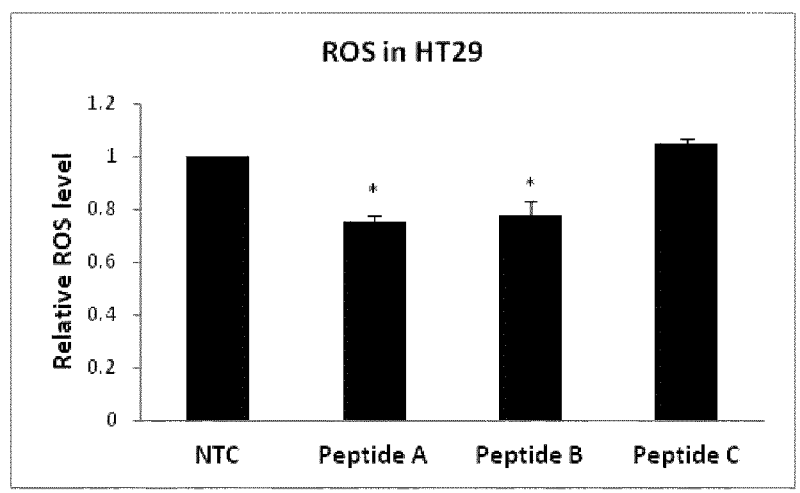

ROS level in primary human keratinocytes treated with 10 or 50 µM of peptides A, B, and C for 24 h were assayed using the CM-H2DCF-DA probes (FIG. 2A). A significant decrease in ROS level was observed in cells treated with Nox1 inhibitor peptides A and B. To examine the specificity of these peptides, the ROS levels were assessed in human colon adenocarcinoma HT29 cell line in which Nox1 is the only active member of Nox family. Measurement of ROS level in HT29 cells showed that treatment with Nox1 inhibitor peptides A and B resulted in a significant reduction in ROS level, suggesting a specific inhibitory effect of these peptides on Nox1 activity (FIG. 2B).

Figure 3A:
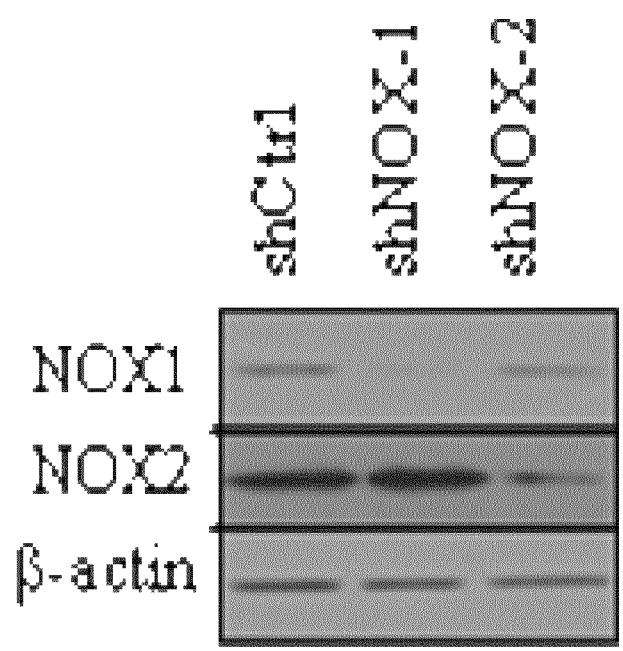
FIGS. 3A, 3B and 3C: show inhibition of endogenous Nox1 and Nox2 protein expression using lentivirus-mediated expression of shRNA against Nox1 and Nox2. Keratinocytes were transduced with different shRNA (shNox1, shNox2 and the control shCtrl). Transduction efficacy was checked by western blotting analysis.
Figure 3B:
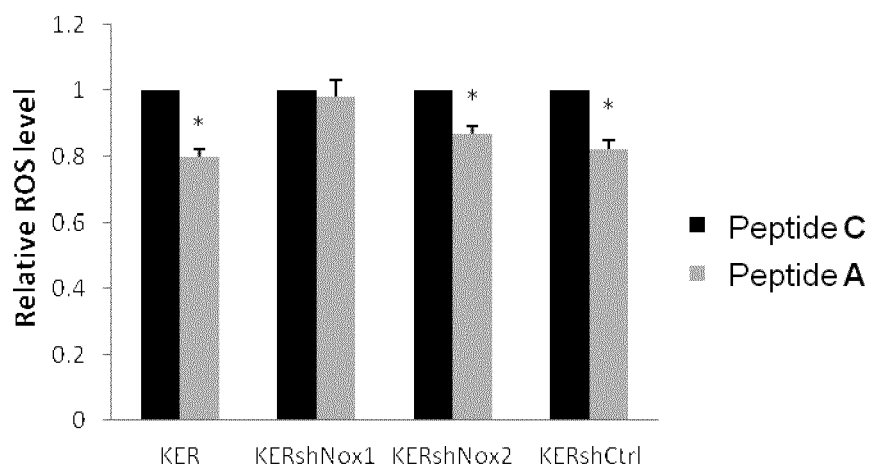
Figure 3C:
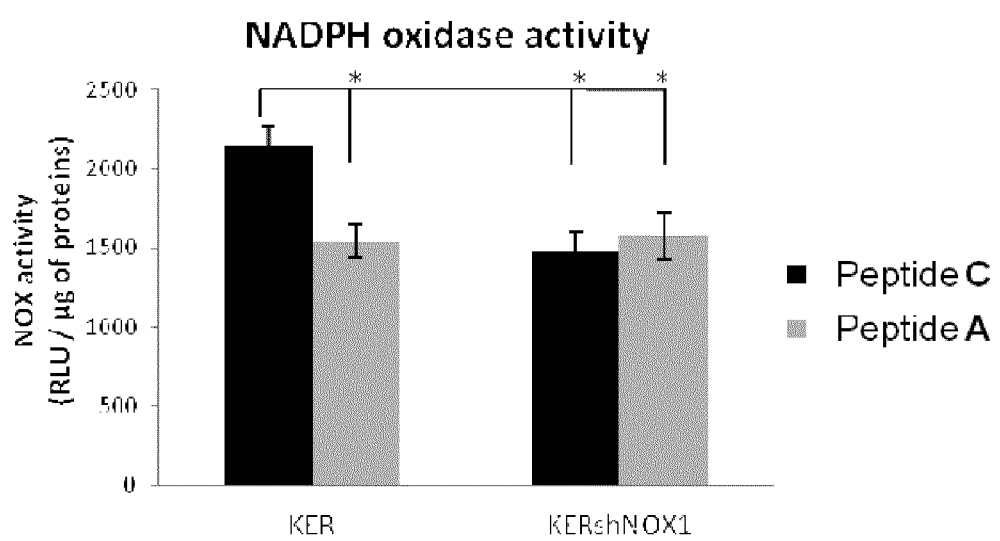

To examine the specificity of these peptides, the expression of endogenous Nox1 and Nox2 protein was inhibited using lentivirus-mediated expression of shRNA against Nox1 and Nox2. Both shNox1 and shNox2 stably inhibited more than 80% of Nox1 and Nox2 expression, respectively (FIG. 3A). shCtrl, shNox1 or shNox2-transduced keratinocytes were then treated with peptide A. Measures of ROS level revealed that treatment with peptide A had no effect on steady-state levels of ROS in shNox1-transduced cells, thus showing that peptide A blocked Nox1-dependent ROS generation with very high (near 100%) efficiency and specificity (FIG. 3B). Further, NADPH oxidase activity was measured in shCtrl and shNox1-transduced cells treated with or without peptide A (FIG. 3C). Equally decreased NADPH oxidase activity was found in shNox1 transduced cells, peptide A-treated cells and shNox1-transduced cells treated with peptide A, thereby demonstrating the efficiency and specificity of peptide A to block Nox1 activation.

Example 1—In Vivo Evaluation of the Nox1 Inhibitor Peptides

Figure 4A:
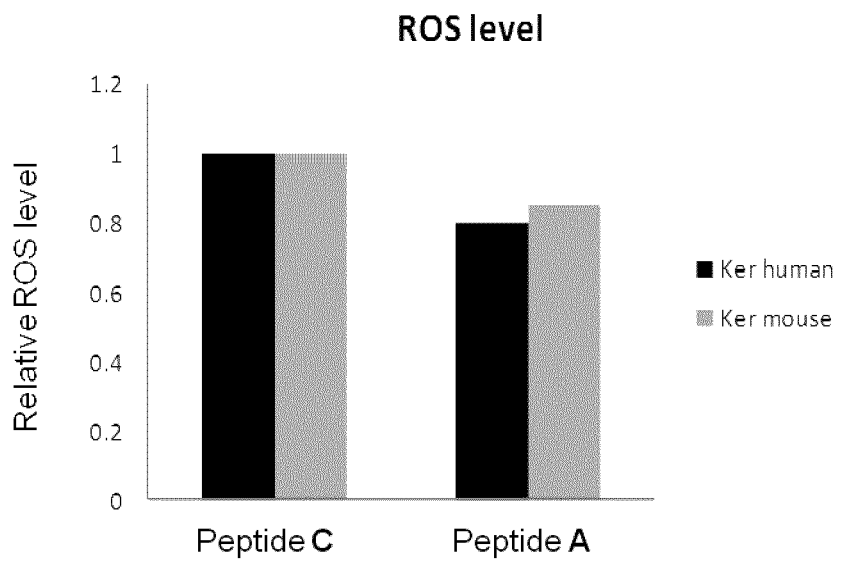
FIGS. 4A, 4B, and 4C: show the inhibition of ROS production and NADPH oxidase activity and thus the photo protection effect on human and murin keratinocytes of Nox1 inhibitor peptide A. Keratinocytes isolated from human biopsies (Ker human) and mouse epidermis (Ker mouse) were treated with 10 µM of either Nox1 inhibitor peptide A or control scramble peptide C. The ROS level (4A) and the NADPH oxidase activity (4B) were measured 24 h post-treatment. The activity of NADPH oxidase in both human and mouse keratinocytes treated with control scramble peptide (C) was arbitrarily set to 100%. The % of inhibition of NADPH oxidase activity upon treatment with Nox1 inhibitor peptide A was then assessed (4C).
Figure 4B:
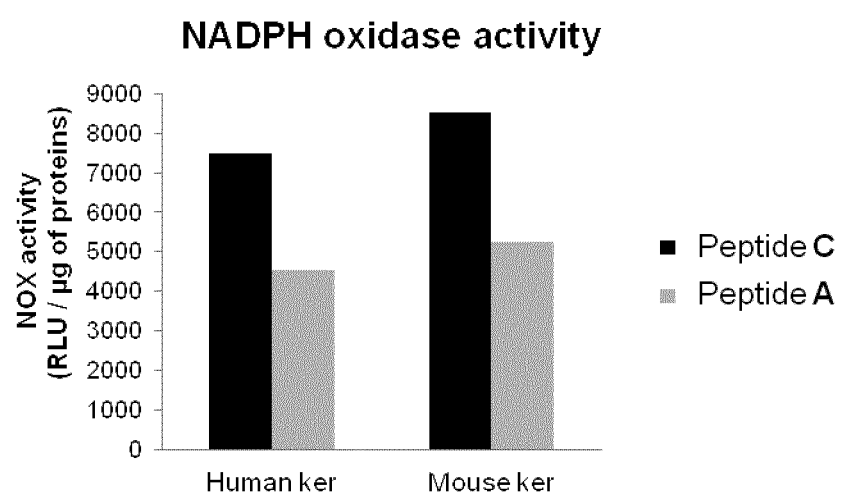
Figure 4C:
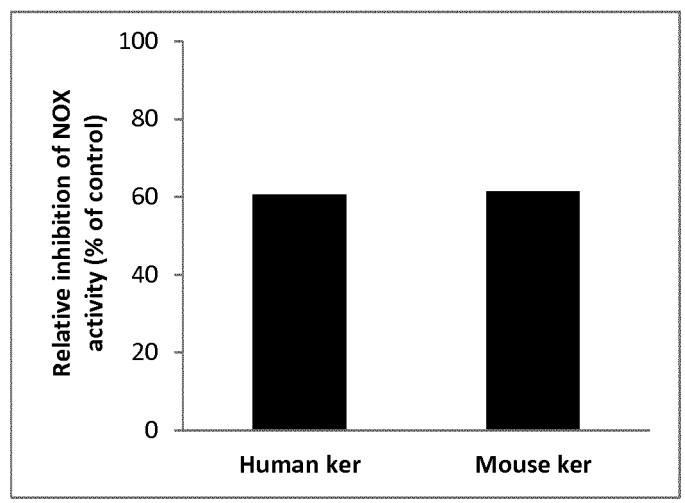

To evaluate the photoprotection effect of Nox1 inhibitor peptide A, it was first examined whether this peptide had an inhibitory effect on Nox1-induced ROS generation in mouse and human keratinocytes (FIG. 4). Results showed a similar preventive effect of peptide A on Nox1-induced ROS generation and Nox activity in mouse and human keratinocytes.

To examine the effect of peptide A on Nox1 activity in mouse skin, SKH-1 mice were treated topically with different doses of peptide A (FIG. 5A). Results showed that peptide A inhibited efficiently Nox activity for up to 3 days when administrated at 3 and 12 mg/kg. The effect of peptide A on UVB irradiated mice was then tested (FIG. 5B). Results showed that topical treatment with peptide A 10 min prior to irradiation efficiently blocked UVB-induced Nox activation in mice treated with 3 and 12 mg/kg.

To examine the photoprotective effects of peptide A, the effect of peptide A administration on UVB-induced squamous cell carcinomas (SCC) induction using SKH-1 hairless mice, a well-defined murine model for the study of photocarcinogenesis that develops skin tumors including benign papilloma and malignant SCC. The validity of this model is exemplified by the remarkable similarity between UVB-induced carcinogenesis in these mice and the UV carcinogenesis pathway in human skin. SKH-1 hairless mice have yield extremely valuable data on the dose, time-course and the action spectrum for skin tumorigenesis following chronic UV B irradiation. In this study, peptide A (3 mg/kg) was administrated three times per week and 10 minutes prior to each UV B exposure. Results showed that treatment with peptide A resulted in a decrease of 2.3 and 2.9 times in tumor number and tumor size, respectively (FIGS. 6A and 6B). Furthermore, 57% of the tumors in peptide A-treated mice had a volume less than 5 mm$^3$ compared to only 8% in the mice treated with control peptide C (FIG. 6C).

Measures of NADPH oxidase activity in mouse tumors showed a significant efficiency of peptide A in prevention of Nox activity (FIG. 7). The activity of NADPH oxidase was reduced 70% in non-tumor bearing skin and 54% in tumors isolated from mice treated with peptide A compared with vehicle treated mice (FIG. 7).

Example 2—Effect of Nox1 Inhibitor Peptides in Cancer Therapy

TABLE 6

| Diseases | Test In vitro | In Vivo |
|---|---|---|
| Basal cell carcinoma | | Ptch1+/− mice model |
| Skin spino-cellular carcinoma | A431, SCC-12, SCC-15 | SKH-1 mice |
| melanoma | WM35, WM9, WM3629 | tyr-BRAF$^{V600E}$ and tyr-BRAF$^{V600E}$/PTEN$^{-/-}$ mice models |
| Acute lymphoblastic leukemia (ALL) | MOLT4, CCL-119, CCL-120 | |
| Acute myeloid leukemia (AML) | CCL-246, THP1, HL60 | |
| Chronic myeloid leukemia (CML) | K562, AR230, LAMA84 | |
| pancreatic cancer | Capan-2, PaCa-3, CRL-1687 | |
| prostate cancer | PC-3, PC-93, DU-145, LNCaP | |
| colorectal carcinoma | HT-29, HT-115, MDST8, CACO-2 | |
| ovarien cancer | PA-I, A2780, A2774, OVCAR-3, SW626 | |
| Lymphoma | Raji, CCL-113 | |

Example 2.1: In Vitro Effect on Cancer Cell Lines

The effect of Nox1 inhibition is assessed on different cell lines as listed in Table 6. Cell proliferation, cell cycle progression and apoptosis may be compared between non-treated cells and cells which are treated with Nox1 inhibitor peptides.

Example 2.2: Xenografts of Cells into NOD/SCID Mice

Cells are trypsinized, washed in DPBS, and resuspended in DPBS with 25% Matrigel (BD Biosciences). 2×10$^6$ cells are injected subcutaneously into 6 to 8 weeks old NOD/SCID mice (The Jackson Laboratory). For each cell line, mice are divided into two groups: one treated with vehicle and the other is treated with a Nox1 inhibitor peptide. Tumor formation and tumor growth is monitored up to two months. Each tumor is dissected, measured, fixed in 4% paraformaldehyde, embedded in paraffin, and processed for H&E staining. Proliferation rate and apoptosis rate are evaluated.

Example 2.3: Mice Models

Effects of Nox1 inhibitor peptides on skin tumors are tested using following models: spontaneous and UVB-induced BCC in Patch mice; UVB-induced SCC in SKH-1; and spontaneous melanoma formation in BRAF mice. For each models, mice are divided into two groups: one treated with vehicle and other treated with Nox1 inhibitor peptides.

Example 3—Effect of Nox1 Inhibitor Peptides on Inflammatory and Auto-Immune Diseases

TABLE 7

| Inflammatory and auto-immune diseases | arthritis | PBL-derived macrophage | Chronic arthritis Rat model |
|---|---|---|---|
| | asthma | IgE-DNP-induced inflammation | Rat ear hypersensitivity |

Example 3.1: In Vitro Effects

Nox1 inhibitor peptides are tested on arthritis, periphery blood lymphocyte (PBL)-derived macrophages is activated in presence and absence of Nox1 inhibitor peptides. Secretion of different inflammatory mediators (TNF-α, IL-6, IL-1β, IL-8, IL-10) is detected.

Effects of Nox1 inhibitor peptides are also tested on asthma by assessing IgE-DNP-induced inflammation is tested in presence and absence of Nox1 inhibitor peptides.

Example 3.2: In Vivo Effects

Rat model of arthritis is treated with different doses of Nox1 inhibitor peptides to evaluate peptide amelioration of clinical scores and prevention of bone destruction.

Furthermore, the efficiency of Nox1 inhibitor peptides in asthma, rat ear hypersensitivity is tested in presence and absence of Nox1 inhibitor peptides.

Example 4—Effect of Nox1 Inhibitor Peptides on Angiogenesis

TABLE 8

| Normal angiogenesis | Endothelial cell migration and tube-like structure formation using HUVEC | Study of skin angiogenesis in C57BL/6 and SKH-1 mice model treated with vehicle or NOX1 inhibitors |
|---|---|---|
| Tumor angiogenesis | | In vivo matrigel angiogenesis assays using mice, Tumor angiogenesis using xenograft models |

To evaluate the effect of Nox1 inhibitor peptides on normal angiogenesis in vitro, endothelial cell migration and tube-like structure formation using HUVEC is tested.

To evaluate the effect of Nox1 inhibitor peptides on normal angiogenesis in vivo, skin angiogenesis in C57BL/6 and SKH-1 mice model, treated with vehicle or Nox1 inhibitor peptides, is examined.

To evaluate the effect of Nox1 inhibitor peptides on tumor angiogenesis, matrigel angiogenesis assay, xenograft models may be used. The various cell lines as listed in Table 6 may be injected into the mice and angiogenesis may be then compared between mice treated with vehicle and Nox1 inhibitor peptides.

Example 5—Effect of Nox1 Inhibitor Peptides on Vascular and Cardiovascular Disorders

TABLE 9

| | |
|---|---|
| Hemangioma | Polyoma middle T-transformed endothelial cells |
| hypertension and the like | Hypertension mediated by infusion of Angiotensin-II into mice |

The effect of Nox1 inhibitor peptides on hemangioma, transformation of endothelial cells by the middle T antigen of murine Polyomavirus (PymT) is tested in the presence or absence of Nox1 inhibitor peptides.

Also, the effect of Nox1 inhibitor peptides is assessed on hypertension, hypertension induction following infusion of angiotensin-II in presence and absence of Nox1 inhibitor peptides.

Example 6—Effect of Nox1 Inhibitor Peptides on Neurodegenerative Disorders

TABLE 10

| | | |
|---|---|---|
| Parkinson's disease | Neuronal cells derived from skin cells through iPS technology | |
| Alzheimer's disease | Neuronal cells derived from skin cells through iPS technology | |
| Multiple sclerosis | | Mouse models of experimental autoimmune encephalomyelitis (EAE) such as PLP139-151 peptide-induced EAE model in SJL Mice |

To evaluate the effect of Nox1 inhibitor peptides on Parkinson and Alzheimer's disease, neuronal cells derived from skin cells through iPS technology is used. The effects of Nox1 inhibitor peptides on ROS levels of neuronal cells derived from patients and healthy skin are also tested.

The effect of Nox1 inhibitor peptides is assessed on multiple sclerosis, mouse models of experimental autoimmune encephalomyelitis (EAE). In fact, PLP139-151 peptide-induced EAE model in SJL mice is used.

Example 7—Effect of NOX1 Inhibitors on Skin Disorders

TABLE 11

| | | |
|---|---|---|
| Atopic dermatitis | IgE-induced keratinocytes | IgE ear hypersensitivity |
| Vitiligo | Reconstructed epidermis, primary keratinocytes and melanocytes | |
| ROS induced skin aging | Keratinocytes, reconstructed epidermis | |

The effects of Nox1 inhibitor peptides are assessed on atopic dermatitis, secretion of inflammatory mediators by IgE-induced activated keratinocytes in presence and absence of Nox1 inhibitor peptides. IgE-induced ear hypersensitivity is also tested in presence and absence of Nox1 inhibitor peptides.

To evaluate the effects of Nox1 inhibitor peptides on Vitiligo, melanocyte detachment may be tested using reconstructed epidermis and primary melanocytes.

Finally, the anti-aging effects of Nox1 inhibitor peptides are tested on primary keratinocytes and reconstructed epidermis. Differentiation and senescence markers are compared between cells treated with vehicle or Nox1 inhibitor peptides.

Example 8—Effect of NOX1 Inhibitor Peptides on Skin Aging

To assess the anti-aging effects of Nox1 inhibitor peptide A (SEQ ID NO: 41) the accelerated aging in XPC deficient mice was first evaluated. To this end, the expression of progerin, a truncated version of lamin A protein involved in progeria syndrome, has been evaluated in 4 months old (young) and 1.5 year old (old) proficient and deficient XPC mice ($XPC^{+/+}$ and $XPC^{-/-}$, respectively) (FIGS. 9A and 9B). Results showed that the progerin level was increased with age and that its expression was higher in $XPC^{-/-}$ mice than wild type mice.

To examine whether this phenotype is related to the overactivation of NADPH oxidase, the activity of NADPH oxidase has been first measured in mouse skin (FIG. 10A). Results revealed that NOX activity was increased with age and that it was also higher in $XPC^{-/-}$ mice than wild type counterparts. Since several studies reveal a wide spectrum of alterations in mitochondria and mitochondrial DNA (mtDNA) including increased disorganization of mitochondrial structure, decline in mitochondrial oxidative phosphorylation (OXPHOS) function and accumulation of mtDNA mutation with aging, the expression level of OXPHOS proteins was then compared among young and old $XPC^{-/-}$ and $XPC^{+/+}$ mice (FIG. 10B). Results indicated a marked decrease in the expression of the complex I, II and III in the old wild type mice compared to the young counterparts. Furthermore, the expression level of these complexes in young $XPC^{-/-}$ was as low as the old wild type mice, correlating with the premature aging in $XPC^{-/-}$ mice.

To investigate the role of NADPH oxidase activity on premature aging in XPC deficient mice, one month old $XPC^{+/+}$ and $XPC^{-/-}$ mice have been treated with NOX1 inhibitor peptide or vehicle three times per week for three months. The progerin expression (FIG. 11), OXPHOS protein expression (FIG. 12) and metabolism profile in murine epidermal cells have been then evaluated. Results showed that inhibition of NOX1 activity diminished the accelerated aging in XPC deficient mice. In fact, NOX1 inhibition blocked the increase in protein expression of progerin (FIG. 11) and abrogated the decrease in the expression of OXPHOS complexes I, II and III (FIG. 12). To have a general idea on the effects of NOX1 peptide inhibitor on the XPC knockdown-induced metabolism alteration, proteomic approach has been used. Results showed that there was a significant reduction in the expression of several proteins involving in pentose phosphate pathway, TCA cycle, mitochondrial OXPHOS and fatty acid β-oxidation. Treatment of mice with NOX1 inhibitor peptide eliminated the effects of XPC deficiency on metabolic alteration.

All these experiments have been performed with Nox1 inhibitor peptide as set forth in SEQ ID NO: 2 and the same results have been obtained.

Altogether, these results indicated that NOX1 inhibitor peptide A as well as NOX1 inhibitor peptide as set forth in SEQ ID NO: 2 blocked XPC deficiency-induced premature aging.

The invention claimed is:

1. A peptide consisting of a sequence having at least 90% sequence identity to any of the following sequences:

```
PPTVPTR    (SEQ ID NO: 2)
PPSVPTR    (SEQ ID NO: 3)
PPMVPTR    (SEQ ID NO: 4)
PPCVPTR    (SEQ ID NO: 5)
PPPVPTR    (SEQ ID NO: 6)
PPAVPTR    (SEQ ID NO: 7)
PPVVPTR    (SEQ ID NO: 8)
PPTVPSR    (SEQ ID NO: 9)
PPTVPMR    (SEQ ID NO: 10)
PPTVPVR    (SEQ ID NO: 11)
PPTVPAR    (SEQ ID NO: 12)
QPTAPTR    (SEQ ID NO: 13)
PPTLPTR    (SEQ ID NO: 14)
PPTIPTR    (SEQ ID NO: 15)
PPTAPTR    (SEQ ID NO: 16)
PPKVPTR    (SEQ ID NO: 17)
QPTVPTR    (SEQ ID NO: 18)
APTVPTR    (SEQ ID NO: 19)
PPTVPTRPS  (SEQ ID NO: 20)
IQSRCCTVT  (SEQ ID NO: 21)
PTVPTRP    (SEQ ID NO: 22)
TVPTRPS    (SEQ ID NO: 23)
RPSPGAI    (SEQ ID NO: 24)
SPGAIQS    (SEQ ID NO: 25)
PGAIQSR    (SEQ ID NO: 26)
GAIQSRC    (SEQ ID NO: 27)
AIQSRCC    (SEQ ID NO: 28)
IQSRCCT    (SEQ ID NO: 29)
QSRCCTV    (SEQ ID NO: 30)
SRCCTVT    (SEQ ID NO: 31)
QVVAQHSYSA (SEQ ID NO: 32)
QGPEDLGFRQ (SEQ ID NO: 33)
LGFRQGDTVD (SEQ ID NO: 34)
GDTVDVLCEE (SEQ ID NO: 35)
VLCEEPDVPL (SEQ ID NO: 36)
PDVPLAVDQA (SEQ ID NO: 37)
AVDQAWLEGH (SEQ ID NO: 38).
```

2. The peptide of claim 1, wherein said peptide has 100% sequence identity to any of SEQ ID NOs: 2-38.

3. A composition comprising the peptide of claim 1.

4. A pharmaceutical composition comprising the composition of claim 3 and one or more pharmaceutically acceptable carrier(s).

5. A method of decreasing the levels of reactive oxygen species (ROS) and/or inhibiting production of reactive oxygen species (ROS), and/or selectively reducing and/or inhibiting NADPH oxidase 1 (Nox1) activity in a subject in need thereof, comprising administering to the subject the peptide of claim 1 parenterally or topically.

6. The method of claim 5, wherein NADPH oxidase 1 (Nox1) activity selectively is reduced by at least 20%, or at least 30%, or at least 35%, 40%, 45%, 50%, 54%, 55%, 56%, 57%, 58%, 59%, 60% or 100%.

7. A method for providing protection against UV-radiation or for enhancing photo protection to both UVA and UVB rays in a subject in need thereof, comprising applying to the skin of the subject the peptide of claim 1.

8. A method of treating and/or repairing skin, mucous membranes, scalp and/or hair of a subject in need thereof, comprising applying to the skin, mucous membranes, scalp and/or hair of the subject the peptide of claim 1.

9. A method of reducing or postponing skin conditions due to aging, photo-aging, and skin conditions due to premature aging in a subject in need thereof, comprising applying to the skin of the subject the peptide of claim 1.

10. A method of treating diabetic nephropathy, atherosclerosis, asthma, chronic obstructive pulmonary disease (COPD), skin conditions due to aging, or premature aging of the skin in a subject in need thereof, comprising administering to said subject the peptide of claim 1 parenterally or topically.

11. A method of treating cancer in a subject in need thereof, comprising administering to said subject the peptide of claim 1 parenterally or topically, wherein said cancer is caused by xeroderma pigmentosum (XP) gene mutation or RAS mutation.

12. The method of claim 11, wherein said cancer is a skin cancer selected from squamous cell carcinoma or basal cell carcinoma.

13. A method of treating atherosclerosis or diabetic nephropathy in a subject in need thereof, comprising administering to said subject the peptide of claim 1 parenterally or topically.

14. A method of treating a neurodegenerative disorder in a subject in need thereof, comprising administering to said subject the peptide of claim 1 parenterally or topically, wherein said neurodegenerative disorder is selected from the group consisting of Parkinson's disease, Alzheimer's disease and multiple sclerosis.

* * * * *

```
                          SEQUENCE LISTING

<160> NUMBER OF SEQ ID NOS: 57

<210> SEQ ID NO 1
<211> LENGTH: 7
<212> TYPE: PRT
<213> ORGANISM: ARTIFICIAL SEQUENCE
<220> FEATURE:
<223> OTHER INFORMATION: GENERAL AMINO ACID FORMULA
<220> FEATURE:
<221> NAME/KEY: variant
<222> LOCATION: (1)
<223> OTHER INFORMATION: Xaa = Ala, Pro or Gln
<220> FEATURE:
<221> NAME/KEY: variant
<222> LOCATION: (3)
<223> OTHER INFORMATION: Xaa = Pro, Thr, Val, Ala, Ser, Cys, Met or Lys
<220> FEATURE:
<221> NAME/KEY: variant
<222> LOCATION: (4)
<223> OTHER INFORMATION: Xaa = Leu, Ile, Val or Ala
<220> FEATURE:
<221> NAME/KEY: variant
<222> LOCATION: (6)
<223> OTHER INFORMATION: Xaa = Thr, Val, Ser, Ala or Met

<400> SEQUENCE: 1

Xaa Pro Xaa Xaa Pro Xaa Arg
1               5

<210> SEQ ID NO 2
<211> LENGTH: 7
<212> TYPE: PRT
<213> ORGANISM: HOMO SAPIENS

<400> SEQUENCE: 2

Pro Pro Thr Val Pro Thr Arg
1               5

<210> SEQ ID NO 3
<211> LENGTH: 7
<212> TYPE: PRT
<213> ORGANISM: HOMO SAPIENS

<400> SEQUENCE: 3

Pro Pro Ser Val Pro Thr Arg
1               5

<210> SEQ ID NO 4
<211> LENGTH: 7
<212> TYPE: PRT
<213> ORGANISM: HOMO SAPIENS

<400> SEQUENCE: 4

Pro Pro Met Val Pro Thr Arg
1               5

<210> SEQ ID NO 5
<211> LENGTH: 7
<212> TYPE: PRT
<213> ORGANISM: HOMO SAPIENS

<400> SEQUENCE: 5

Pro Pro Cys Val Pro Thr Arg
```

```
<210> SEQ ID NO 6
<211> LENGTH: 7
<212> TYPE: PRT
<213> ORGANISM: HOMO SAPIENS

<400> SEQUENCE: 6

Pro Pro Pro Val Pro Thr Arg
1               5

<210> SEQ ID NO 7
<211> LENGTH: 7
<212> TYPE: PRT
<213> ORGANISM: HOMO SAPIENS

<400> SEQUENCE: 7

Pro Pro Ala Val Pro Thr Arg
1               5

<210> SEQ ID NO 8
<211> LENGTH: 7
<212> TYPE: PRT
<213> ORGANISM: HOMO SAPIENS

<400> SEQUENCE: 8

Pro Pro Val Val Pro Thr Arg
1               5

<210> SEQ ID NO 9
<211> LENGTH: 7
<212> TYPE: PRT
<213> ORGANISM: HOMO SAPIENS

<400> SEQUENCE: 9

Pro Pro Thr Val Pro Ser Arg
1               5

<210> SEQ ID NO 10
<211> LENGTH: 7
<212> TYPE: PRT
<213> ORGANISM: HOMO SAPIENS

<400> SEQUENCE: 10

Pro Pro Thr Val Pro Met Arg
1               5

<210> SEQ ID NO 11
<211> LENGTH: 7
<212> TYPE: PRT
<213> ORGANISM: HOMO SAPIENS

<400> SEQUENCE: 11

Pro Pro Thr Val Pro Val Arg
1               5

<210> SEQ ID NO 12
<211> LENGTH: 7
<212> TYPE: PRT
<213> ORGANISM: HOMO SAPIENS

<400> SEQUENCE: 12

Pro Pro Thr Val Pro Ala Arg
1               5
```

```
<210> SEQ ID NO 13
<211> LENGTH: 7
<212> TYPE: PRT
<213> ORGANISM: HOMO SAPIENS

<400> SEQUENCE: 13

Gln Pro Thr Ala Pro Thr Arg
1               5

<210> SEQ ID NO 14
<211> LENGTH: 7
<212> TYPE: PRT
<213> ORGANISM: HOMO SAPIENS

<400> SEQUENCE: 14

Pro Pro Thr Leu Pro Thr Arg
1               5

<210> SEQ ID NO 15
<211> LENGTH: 7
<212> TYPE: PRT
<213> ORGANISM: HOMO SAPIENS

<400> SEQUENCE: 15

Pro Pro Thr Ile Pro Thr Arg
1               5

<210> SEQ ID NO 16
<211> LENGTH: 7
<212> TYPE: PRT
<213> ORGANISM: HOMO SAPIENS

<400> SEQUENCE: 16

Pro Pro Thr Ala Pro Thr Arg
1               5

<210> SEQ ID NO 17
<211> LENGTH: 7
<212> TYPE: PRT
<213> ORGANISM: HOMO SAPIENS

<400> SEQUENCE: 17

Pro Pro Lys Val Pro Thr Arg
1               5

<210> SEQ ID NO 18
<211> LENGTH: 7
<212> TYPE: PRT
<213> ORGANISM: HOMO SAPIENS

<400> SEQUENCE: 18

Gln Pro Thr Val Pro Thr Arg
1               5

<210> SEQ ID NO 19
<211> LENGTH: 7
<212> TYPE: PRT
<213> ORGANISM: HOMO SAPIENS

<400> SEQUENCE: 19

Ala Pro Thr Val Pro Thr Arg
1               5

<210> SEQ ID NO 20
```

```
<211> LENGTH: 9
<212> TYPE: PRT
<213> ORGANISM: HOMO SAPIENS

<400> SEQUENCE: 20

Pro Pro Thr Val Pro Thr Arg Pro Ser
1               5

<210> SEQ ID NO 21
<211> LENGTH: 9
<212> TYPE: PRT
<213> ORGANISM: HOMO SAPIENS

<400> SEQUENCE: 21

Ile Gln Ser Arg Cys Cys Thr Val Thr
1               5

<210> SEQ ID NO 22
<211> LENGTH: 7
<212> TYPE: PRT
<213> ORGANISM: HOMO SAPIENS

<400> SEQUENCE: 22

Pro Thr Val Pro Thr Arg Pro
1               5

<210> SEQ ID NO 23
<211> LENGTH: 7
<212> TYPE: PRT
<213> ORGANISM: HOMO SAPIENS

<400> SEQUENCE: 23

Thr Val Pro Thr Arg Pro Ser
1               5

<210> SEQ ID NO 24
<211> LENGTH: 7
<212> TYPE: PRT
<213> ORGANISM: HOMO SAPIENS

<400> SEQUENCE: 24

Arg Pro Ser Pro Gly Ala Ile
1               5

<210> SEQ ID NO 25
<211> LENGTH: 7
<212> TYPE: PRT
<213> ORGANISM: HOMO SAPIENS

<400> SEQUENCE: 25

Ser Pro Gly Ala Ile Gln Ser
1               5

<210> SEQ ID NO 26
<211> LENGTH: 7
<212> TYPE: PRT
<213> ORGANISM: HOMO SAPIENS

<400> SEQUENCE: 26

Pro Gly Ala Ile Gln Ser Arg
1               5

<210> SEQ ID NO 27
<211> LENGTH: 7
<212> TYPE: PRT
```

```
<213> ORGANISM: HOMO SAPIENS

<400> SEQUENCE: 27

Gly Ala Ile Gln Ser Arg Cys
1               5

<210> SEQ ID NO 28
<211> LENGTH: 7
<212> TYPE: PRT
<213> ORGANISM: HOMO SAPIENS

<400> SEQUENCE: 28

Ala Ile Gln Ser Arg Cys Cys
1               5

<210> SEQ ID NO 29
<211> LENGTH: 7
<212> TYPE: PRT
<213> ORGANISM: HOMO SAPIENS

<400> SEQUENCE: 29

Ile Gln Ser Arg Cys Cys Thr
1               5

<210> SEQ ID NO 30
<211> LENGTH: 7
<212> TYPE: PRT
<213> ORGANISM: HOMO SAPIENS

<400> SEQUENCE: 30

Gln Ser Arg Cys Cys Thr Val
1               5

<210> SEQ ID NO 31
<211> LENGTH: 7
<212> TYPE: PRT
<213> ORGANISM: HOMO SAPIENS

<400> SEQUENCE: 31

Ser Arg Cys Cys Thr Val Thr
1               5

<210> SEQ ID NO 32
<211> LENGTH: 10
<212> TYPE: PRT
<213> ORGANISM: HOMO SAPIENS

<400> SEQUENCE: 32

Gln Val Val Ala Gln His Ser Tyr Ser Ala
1               5                   10

<210> SEQ ID NO 33
<211> LENGTH: 10
<212> TYPE: PRT
<213> ORGANISM: HOMO SAPIENS

<400> SEQUENCE: 33

Gln Gly Pro Glu Asp Leu Gly Phe Arg Gln
1               5                   10

<210> SEQ ID NO 34
<211> LENGTH: 10
<212> TYPE: PRT
<213> ORGANISM: HOMO SAPIENS
```

```
<400> SEQUENCE: 34

Leu Gly Phe Arg Gln Gly Asp Thr Val Asp
1               5                   10

<210> SEQ ID NO 35
<211> LENGTH: 10
<212> TYPE: PRT
<213> ORGANISM: HOMO SAPIENS

<400> SEQUENCE: 35

Gly Asp Thr Val Asp Val Leu Cys Glu Glu
1               5                   10

<210> SEQ ID NO 36
<211> LENGTH: 10
<212> TYPE: PRT
<213> ORGANISM: HOMO SAPIENS

<400> SEQUENCE: 36

Val Leu Cys Glu Glu Pro Asp Val Pro Leu
1               5                   10

<210> SEQ ID NO 37
<211> LENGTH: 10
<212> TYPE: PRT
<213> ORGANISM: HOMO SAPIENS

<400> SEQUENCE: 37

Pro Asp Val Pro Leu Ala Val Asp Gln Ala
1               5                   10

<210> SEQ ID NO 38
<211> LENGTH: 10
<212> TYPE: PRT
<213> ORGANISM: HOMO SAPIENS

<400> SEQUENCE: 38

Ala Val Asp Gln Ala Trp Leu Glu Gly His
1               5                   10

<210> SEQ ID NO 39
<211> LENGTH: 16
<212> TYPE: PRT
<213> ORGANISM: ARTIFICIAL SEQUENCE
<220> FEATURE:
<223> OTHER INFORMATION: FUSION PEPTIDE

<400> SEQUENCE: 39

Arg Lys Lys Arg Arg Gln Arg Arg Pro Pro Thr Val Pro Thr Arg
1               5                   10                  15

<210> SEQ ID NO 40
<211> LENGTH: 16
<212> TYPE: PRT
<213> ORGANISM: ARTIFICIAL SEQUENCE
<220> FEATURE:
<223> OTHER INFORMATION: FUSION PEPTIDE

<400> SEQUENCE: 40

Arg Arg Arg Arg Arg Arg Arg Arg Arg Pro Pro Thr Val Pro Thr Arg
1               5                   10                  15

<210> SEQ ID NO 41
<211> LENGTH: 18
<212> TYPE: PRT
```

<213> ORGANISM: ARTIFICIAL SEQUENCE
<220> FEATURE:
<223> OTHER INFORMATION: FUSION PEPTIDE

<400> SEQUENCE: 41

Arg Lys Lys Arg Arg Gln Arg Arg Pro Pro Thr Val Pro Thr Arg
1               5                   10                  15

Pro Ser

<210> SEQ ID NO 42
<211> LENGTH: 18
<212> TYPE: PRT
<213> ORGANISM: ARTIFICIAL SEQUENCE
<220> FEATURE:
<223> OTHER INFORMATION: FUSION PEPTIDE

<400> SEQUENCE: 42

Arg Lys Lys Arg Arg Gln Arg Arg Ile Gln Ser Arg Cys Cys Thr
1               5                   10                  15

Val Thr

<210> SEQ ID NO 43
<211> LENGTH: 18
<212> TYPE: PRT
<213> ORGANISM: ARTIFICIAL SEQUENCE
<220> FEATURE:
<223> OTHER INFORMATION: FUSION PEPTIDE

<400> SEQUENCE: 43

Arg Lys Lys Arg Arg Gln Arg Arg Arg Cys Leu Arg Ile Thr Arg Gln
1               5                   10                  15

Ser Arg

<210> SEQ ID NO 44
<211> LENGTH: 25
<212> TYPE: PRT
<213> ORGANISM: HOMO SAPIENS

<400> SEQUENCE: 44

Pro Pro Thr Val Pro Thr Arg Pro Ser Pro Gly Ala Ile Gln Ser Arg
1               5                   10                  15

Cys Cys Thr Val Thr Arg Arg Ala Leu
            20                  25

<210> SEQ ID NO 45
<211> LENGTH: 65
<212> TYPE: PRT
<213> ORGANISM: HOMO SAPIENS

<400> SEQUENCE: 45

Gln Val Val Ala Gln His Ser Tyr Ser Ala Gln Gly Pro Glu Asp Leu
1               5                   10                  15

Gly Phe Arg Gln Gly Asp Thr Val Asp Val Leu Cys Glu Glu Pro Asp
                20                  25                  30

Val Pro Leu Ala Val Asp Gln Ala Trp Leu Glu Gly His Cys Asp Gly
            35                  40                  45

Arg Ile Gly Ile Phe Pro Lys Cys Phe Val Val Pro Ala Gly Pro Arg
        50                  55                  60

Met
65

```
<210> SEQ ID NO 46
<211> LENGTH: 9
<212> TYPE: PRT
<213> ORGANISM: ARTIFICIAL SEQUENCE
<220> FEATURE:
<223> OTHER INFORMATION: FUSION PEPTIDE

<400> SEQUENCE: 46

Arg Arg Arg Arg Arg Arg Arg Arg Arg
1               5

<210> SEQ ID NO 47
<211> LENGTH: 6
<212> TYPE: PRT
<213> ORGANISM: ARTIFICIAL SEQUENCE
<220> FEATURE:
<223> OTHER INFORMATION: FUSION PEPTIDE

<400> SEQUENCE: 47

Cys Asn Gly Arg Cys Gly
1               5

<210> SEQ ID NO 48
<211> LENGTH: 17
<212> TYPE: PRT
<213> ORGANISM: ARTIFICIAL SEQUENCE
<220> FEATURE:
<223> OTHER INFORMATION: FUSION PEPTIDE

<400> SEQUENCE: 48

Lys Lys Trp Lys Met Arg Arg Asn Gln Phe Trp Val Lys Val Gln Arg
1               5                   10                  15

Gly

<210> SEQ ID NO 49
<211> LENGTH: 27
<212> TYPE: PRT
<213> ORGANISM: ARTIFICIAL SEQUENCE
<220> FEATURE:
<223> OTHER INFORMATION: FUSION PEPTIDE

<400> SEQUENCE: 49

Lys Asn Leu Trp Ala Ala Gln Arg Tyr Gly Arg Glu Leu Arg Arg Met
1               5                   10                  15

Ser Asp Glu Phe Glu Gly Ser Phe Lys Gly Leu
            20                  25

<210> SEQ ID NO 50
<211> LENGTH: 9
<212> TYPE: PRT
<213> ORGANISM: ARTIFICIAL SEQUENCE
<220> FEATURE:
<223> OTHER INFORMATION: FUSION PEPTIDE

<400> SEQUENCE: 50

Arg Lys Lys Arg Arg Gln Arg Arg Arg
1               5

<210> SEQ ID NO 51
<211> LENGTH: 21
<212> TYPE: PRT
<213> ORGANISM: ARTIFICIAL SEQUENCE
<220> FEATURE:
<223> OTHER INFORMATION: SYNTHETIC PEPTIDIC FRAGMENT

<400> SEQUENCE: 51
```

```
Thr Arg Ser Ser Arg Ala Gly Leu Gln Phe Pro Val Gly Arg Val His
1               5                   10                  15

Arg Leu Leu Arg Lys
            20
```

<210> SEQ ID NO 52
<211> LENGTH: 13
<212> TYPE: PRT
<213> ORGANISM: ARTIFICIAL SEQUENCE
<220> FEATURE:
<223> OTHER INFORMATION: SYNTHETIC PEPTIDIC FRAGMENT

<400> SEQUENCE: 52

```
Thr Arg Arg Gln Arg Thr Arg Ala Arg Arg Asn Arg
1               5                   10
```

<210> SEQ ID NO 53
<211> LENGTH: 15
<212> TYPE: PRT
<213> ORGANISM: ARTIFICIAL SEQUENCE
<220> FEATURE:
<223> OTHER INFORMATION: SYNTHETIC PEPTIDIC FRAGMENT

<400> SEQUENCE: 53

```
Lys Lys Ala Ala Ala Val Leu Leu Pro Val Leu Leu Ala Ala Pro
1               5                   10                  15
```

<210> SEQ ID NO 54
<211> LENGTH: 7
<212> TYPE: PRT
<213> ORGANISM: ARTIFICIAL SEQUENCE
<220> FEATURE:
<223> OTHER INFORMATION: SYNTHETIC PEPTIDIC FRAGMENT

<400> SEQUENCE: 54

```
Arg Pro Ala Arg Pro Ala Arg
1               5
```

<210> SEQ ID NO 55
<211> LENGTH: 18
<212> TYPE: PRT
<213> ORGANISM: ARTIFICIAL SEQUENCE
<220> FEATURE:
<223> OTHER INFORMATION: SYNTHETIC PEPTIDIC FRAGMENT

<400> SEQUENCE: 55

```
Arg Gln Ile Lys Ile Trp Phe Gln Asn Arg Arg Met Lys Trp Lys Lys
1               5                   10                  15

Gly Gly
```

<210> SEQ ID NO 56
<211> LENGTH: 8
<212> TYPE: PRT
<213> ORGANISM: ARTIFICIAL SEQUENCE
<220> FEATURE:
<223> OTHER INFORMATION: SYNTHETIC PEPTIDIC FRAGMENT

<400> SEQUENCE: 56

```
Pro Pro Thr Val Pro Thr Arg Pro
1               5
```

<210> SEQ ID NO 57
<211> LENGTH: 18
<212> TYPE: PRT
<213> ORGANISM: ARTIFICIAL SEQUENCE
<220> FEATURE:

<223> OTHER INFORMATION: SYNTHETIC PEPTIDIC FRAGMENT

<400> SEQUENCE: 57

Arg Lys Lys Arg Arg Gln Arg Arg Arg Val Thr Pro Thr Arg Pro Pro
1               5                   10                  15
Ser Arg